US011096968B2

(12) United States Patent
Young

(10) Patent No.: US 11,096,968 B2
(45) Date of Patent: Aug. 24, 2021

(54) USE OF ANTI-AGING GLYCOPROTEIN FOR ENHANCING SURVIVAL OF NEUROSENSORY PRECURSOR CELLS

(71) Applicant: PROTOKINETIX INC., St. Mary's, VA (US)

(72) Inventor: Lachlan Grant Young, Vancouver (CA)

(73) Assignee: Protokinetix Inc., St. Mary's, WV (US)

( * ) Notice: Subject to any disclaimer, the term of this patent is extended or adjusted under 35 U.S.C. 154(b) by 417 days.

(21) Appl. No.: 16/073,282

(22) PCT Filed: Jan. 27, 2017

(86) PCT No.: PCT/IB2017/050444
§ 371 (c)(1),
(2) Date: Jul. 26, 2018

(87) PCT Pub. No.: WO2017/130148
PCT Pub. Date: Aug. 3, 2017

(65) Prior Publication Data
US 2019/0046582 A1 Feb. 14, 2019

Related U.S. Application Data

(60) Provisional application No. 62/287,857, filed on Jan. 27, 2016.

(51) Int. Cl.
A61K 35/30 (2015.01)
A61K 38/14 (2006.01)
A61K 47/42 (2017.01)
A61P 27/00 (2006.01)
A61K 31/16 (2006.01)
A61K 31/164 (2006.01)
C07K 14/00 (2006.01)
C07K 5/08 (2006.01)
C07K 9/00 (2006.01)
A61K 31/335 (2006.01)
C07K 5/10 (2006.01)

(52) U.S. Cl.
CPC ............ A61K 35/30 (2013.01); A61K 31/16 (2013.01); A61K 31/164 (2013.01); A61K 31/335 (2013.01); A61K 38/14 (2013.01); A61P 27/00 (2018.01); C07K 5/08 (2013.01); C07K 5/0827 (2013.01); C07K 9/001 (2013.01); C07K 14/00 (2013.01); C07K 5/1027 (2013.01)

(58) Field of Classification Search
CPC ......... A61K 35/30; A61K 38/14; A61P 27/00; C07K 5/04; C07K 5/08; C07K 5/10
See application file for complete search history.

(56) References Cited

U.S. PATENT DOCUMENTS

| 2007/0003528 A1 | 1/2007 | Consigny et al. |
| 2009/0311203 A1 | 12/2009 | Castelot Deliencourt-Godefroy et al. |
| 2010/0041584 A1* | 2/2010 | Quirion ................. C07K 9/003 514/1.1 |
| 2015/0182495 A1 | 7/2015 | Zambelli et al. |
| 2015/0352155 A1 | 12/2015 | James et al. |

FOREIGN PATENT DOCUMENTS

| WO | WO-9955838 A1 * | 11/1999 | ........... C12N 5/0623 |
| WO | 2006059227 A1 | 6/2006 | |
| WO | WO-2015140178 A1 * | 9/2015 | ............. A61Q 19/00 |

OTHER PUBLICATIONS

Extended European Search Report in 17743819.9 dated Oct. 7, 2019.
Canola K B et al: "Neurogenic potential of retinal precursor cells (Rpcs) transplanted into a model of terminal stages of retinitis pigmentosa", IOVS, vol. 46, No. Suppl. S, 2005, pp. 4161, XP9516035, & Annual Meeting of the Association-For-Research-In-Research-In-Vision-And-Ophthamology; Ft Lauderdale, FL, USA; May 1-5, 2005. ISSN: 0146-0404. (https://iovs.arvojournals.org/article.aspx?articleid=2403586).
Database WPI, Week 201435, Thomson Scientific, London, GB; AN 2014-G56285 XP002794221, & CN 103 571 793 A (Cas Shanghai Biological Sci Inst). Feb. 12, 2014 (Feb. 12, 2014).
Pressmar S et al: "The fate of heterotopically grafted neural precursor cells in the normal and dystrophic adult mouse retina.", Investigative Opthalmology & Visual Science Dec. 2001, vol. 42, No. 13, Dec. 2001 (Dec. 2001), pp. 3311-3319, XP002794219, ISSN: 0146-0404. (https://www.ncbi.nlm.nih.gov/pubmed/11726638).
Seigel Gail M et al.: "Intraocular Transplantation of E1A-Immortalized Retinal Precursor Cells", Cell Transplantation, Sage, US, vol. 7, No. 6, Nov. 1. 1998 (Nov. 1. 1998), pp. 559-566, XP002526859, ISSN: 0963-6897, DOI: 10.1016/S8963-6897(98)00040-2. (https://www.ncbi.nlm.nih.gov/pubmed/9853584).
International Search Report of PCT/IB2017/050444; dated Jul. 7, 2017.
Cavassani, et al. "TLR3 is an endogenous sensor of tissue necrosis during acute inflammatory events." Journal of Experimental Medicine 205, No. 11 (2008): 2609-2621.
Chen, et al. "Mechanisms of rhodopsin inactivation in vivo as revealed by a COOH-terminal truncation mutant." Science 267, No. 5196 (1995): 374-377.
Dunn, et al. "ARPE-19, a human retinal pigment epithelial cell line with differentiated properties." Experimental eye research 62, No. 2 (1996): 155-170.

(Continued)

Primary Examiner — Theodore R. Howell
(74) Attorney, Agent, or Firm — Kilpatrick Townsend & Stockton LLP

(57) ABSTRACT

The present disclosure relates to an in vitro method for enhancing engraftment of neurosensory precursor cell comprising the step of contacting an isolated neurosensory precursor cell prior to a transplantation in a subject in need thereof, with a gem-difluorinated C-glycopeptide compound of general formula I, or a pharmaceutically acceptable base, addition salt with an acid, hydrate or solvate thereof: (I).

13 Claims, 3 Drawing Sheets

(56) References Cited

OTHER PUBLICATIONS

Klassen, "Stem cells in clinical trials for treatment of retinal degeneration." Expert opinion on biological therapy 16, No. 1 (2016): 7-14.

Lukiw, et al. "A2E selectively induces COX-2 in ARPE-19 and human neural cells." Current eye research 31, No. 3 (2006): 259-263.

Ma, et al. "Combining chondroitinase ABC and growth factors promotes the integration of murine retinal progenitor cells transplanted into Rho-/- mice." Molecular vision 17 (2011): 1759.

Mehta, et al. "ATP-stimulated release of interleukin (IL)-1β and IL-18 requires priming by lipopolysaccharide and is independent of caspase-1 cleavage." Journal of Biological Chemistry 276, No. 6 (2001): 3820-3826.

Miyagishi, et al. "Prostaglandin E2-induced cell death is mediated by activation of EP2 receptors in motor neuron-like NSC-34 cells." Journal of pharmacological sciences 121, No. 4 (2013): 347-350.

Ricciotti, et al. "Prostaglandins and inflammation." Arteriosclerosis, thrombosis, and vascular biology 31, No. 5 (2011): 986-1000.

Scaffidi, et al. "Release of chromatin protein HMGB1 by necrotic cells triggers inflammation." Nature 418, No. 6894 (2002): 191.

Singh, et al. "Reversal of end-stage retinal degeneration and restoration of visual function by photoreceptor transplantation." Proceedings of the National Academy of Sciences 110, No. 3 (2013): 1101-1106.

Stone, et al. "Neural repair and neuroprotection with stem cells in ischemic stroke." Brain sciences 3, No. 2 (2013): 599-614.

Takadera, et al. "Prostaglandin E2 induced caspase-dependent apoptosis possibly through activation of EP2 receptors in cultured hippocampal neurons." Neurochemistry international 45, No. 5 (2004): 713-719.

Tovar-Y-Romo, et al. "Endogenous recovery after brain damage: molecular mechanisms that balance neuronal life/death fate." Journal of neurochemistry 136, No. 1 (2016): 13-27.

Warre-Cornish, et al. "Migration, integration and maturation of photoreceptor precursors following transplantation in the mouse retina." Stem cells and development 23, No. 9 (2013): 941-954.

West, et al. "Defining the integration capacity of embryonic stem cell-derived photoreceptor precursors." Stem cells 30, No. 7 (2012): 1424-1435.

Yanai, et al. "Differentiation of human embryonic stem cells using size-controlled embryoid bodies and negative cell selection in the production of photoreceptor precursor cells." Tissue Engineering Part C: Methods 19, No. 10 (2013): 755-764.

Yanai, et al. "Enhanced functional integration of human photoreceptor precursors into human and rodent retina in an ex vivo retinal explant model system." Tissue Engineering Part A 21, No. 11-12 (2015): 1763-1771.

Zhou, et al. "Necroptosis in health and diseases." In Seminars in cell & developmental biology, vol. 35, pp. 14-23. Academic Press, 2014.

* cited by examiner

USE OF ANTI-AGING GLYCOPROTEIN FOR ENHANCING SURVIVAL OF NEUROSENSORY PRECURSOR CELLS

CROSS-REFERENCE TO RELATED APPLICATIONS

This application is a US National Phase application under 35 USC § 371 of PCT/IB2017/050444, filed Jan. 27, 2017, which claims priority from and the benefit of U.S. Provisional Patent Application No. 62/287,857, filed Jan. 27, 2016, the specifications of which are hereby incorporated by reference in their entireties.

BACKGROUND

(a) Field

The subject matter disclosed generally relates to in vitro method for enhancing engraftment of neurosensory precursor cells and in vitro methods for protecting isolated neurosensory precursor cells from prostaglandin E2 toxicity.

(b) Related Prior Art

Cell transplantation is a promising approach to replace tissue lost as a consequence of retinal degenerative diseases. For example, specialized NPCs such as retinal precursor cells are being investigated for use in retinal diseases such as age-related macular degeneration (AMD) and retinitis pigmentosa (RP) (Klassen, 2015). However, it has become evident that the survival and functional integration rate of transplanted NPCs and in particular specialized retinal precursor cells, remains low (1-3% and 3.5%, respectively; Stone et al., 2013 and Warre-Comish et al., 2014). The factors that inhibit transplanted cell engraftment remain largely unknown, in part because many adverse factors could be at play during in vivo experiments. These factors include immune-rejection, sub-optimal type of NPC, trauma during cell delivery, nutritional deficits in the target tissue and toxic compounds secreted from the target tissue (Ma et al., 2011; West et al., 2012; Singh et al., 2013). To highlight one factor, many neurodegenerative tissues undergo necrosis and as such release toxic metabolites such as the by-products of phospholipids released by the porous plasma membrane (e.g. prostaglandins; Ricciotti and FitzGerald, 2011), free nucleic acids (Cavassani et al., 2008) and high mobility group box 1 protein (HMGB1; Scaffidi et al., 2002). The release of such toxic factors is of particular concern as it triggers inflammatory signals which ultimately lead to more cell death (Zhou and Yuan, 2014). Although numerous factors are released from necrotic tissues, prostaglandins and specifically prostaglandin E2 (PGE2) has been shown to stimulate cell death in several cell culture systems. It has been suggested that during necrosis, as cell walls break down, membrane-derived arachidonic acid is released. This occurs with upregulation of the enzyme cyclooxygenase-2 (COX-2) triggered by cell death signalling and leads to the conversion of arachidonic acid to PGE2 (e.g., Ricciotti and FitzGerald, 2011; Takadera et al., 2004 and Miyagishi et al., 2013).

A recently characterized anti-aging glycopeptide (AAGP™) as a potential protective agent, is a small, stable, synthetic analog of anti-freeze protein (AFP). AFP has been shown to protect cells against extreme conditions has been shown to protect cells for example, against exposure to extreme temperatures and ultraviolet irradiation. AAGP™ compounds are gem difluorinated C-glycopeptides which have also been proposed to have applicability under harsh cellular stresses, such as nutrient deprivation, high temperature and cryopreservation, oxidative stress from hydrogen peroxide ($H_2O_2$), UV irradiation, and inflammation. The cytoprotective effect of this AAGP™ compound is tested in isolated NPC.

Therefore, there exists a need in the art for means of improving transplanted NPC engraftment.

SUMMARY

According to an embodiment, there is provided an in vitro method for enhancing engraftment of neurosensory precursor cells comprising the step of:
a) contacting an isolated neurosensory precursor cell prior to a transplantation in a subject in need thereof, with a gem-difluorinated C-glycopeptide compound of general formula I, or a pharmaceutically acceptable base, addition salt with an acid, hydrate or solvate thereof, and then washing the isolated neurosensory precursor cells to remove the compound:

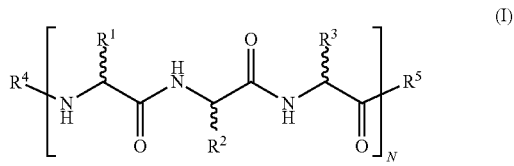

(I)

in which:
N is an integer between 1 and 5,
$R^4$=H, $AA_1$, or $AA_1$-$AA_2$,
$R^5$=OH, $AA_1$, or $AA_1$-$AA_2$,
$AA_1$ and $AA_2$ independently represent amino acids with a non-polar side chain
and
$R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

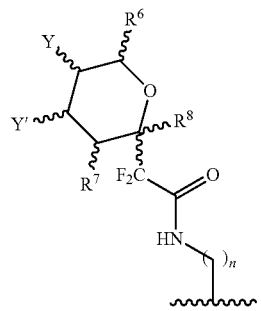

in which:
n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl or acetate group,
R', R" independently=H, alkyl, allyl, benzyl, tosylate group, C(=O)-alkyl or C(=O)—Bn,
R'''=H, alkyl, or acetate group, R[6] is H, CH$_3$, CH$_2$OH, CH$_2$-glycoside group or CH$_2$—OGP in which GP is a protector group selected from alkyl, benzyl, trimethylsilyl, tert-butyldimethylsilyl, tert-butyldiphenylsilyl, or acetate group, R[7]═OH, OGP', NH$_2$, N$_3$, NHGP' or NGP'GP'' in which GP' and GP'' are independently selected from alkyl, benzyl, trimethylsilyl, tert-butyldimethylsilyl, tert-butyldiphenylsilyl, or acetate group, R[8] is a hydrogen atom H or a free or protected alcohol function, and if R[1]═R[2]═H, CH$_3$, CH$_2$Ph, CH(CH$_3$)$_2$, CH$_2$CH(CH$_3$)$_2$, or CH(CH$_3$)CH$_2$CH$_3$ then R[3]═

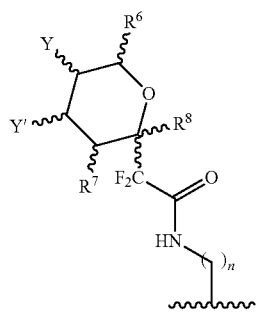

in which: n is an integer between 3 and 4,

Y, Y' are independent groups in which Y, Y'═H, OR, N$_3$, NR'R'', or SR''', where R═H, benzyl, trimethylsilyl, tert-butyldimethylsilyl, tert-butyldiphenylsilyl, or acetate group, R', R'' independently═H, alkyl, allyl, benzyl, tosylate group, C(═O)-alkyl, or C(═O)—Bn, R'''═H, alkyl, or acetate group, R[6] is H, CH$_3$, CH$_2$OH, CH$_2$-glycoside group, or CH$_2$—OGP in which GP is a protector group selected from alkyl, benzyl, trimethylsilyl, tertbutyldimethylsilyl, tert-butyldiphenylsilyl, or acetate group, R[7]═OH, OGP', NH$_2$, N$_3$, NHGP', or NGP'GP'' in which GP' and GP'' are independently selected from alkyl, benzyl, trimethylsilyl, tertbutyldimethylsilyl, tert-butyldiphenylsilyl, or acetate group, R[8] is a hydrogen atom H or a free or protected alcohol function, if R[1]═R[3]═H, CH$_3$, CH$_2$Ph, CH(CH$_3$)$_2$, CH$_2$CH(CH$_3$)$_2$, or CH(CH$_3$)CH$_2$CH$_3$ then R[2]═

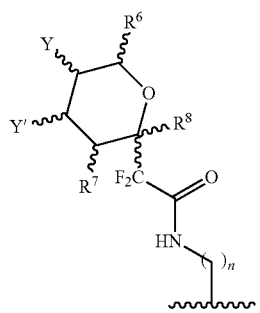

in which: n is an integer between 3 and 4,

Y, Y' are independent groups in which Y, Y'═H, OR, N$_3$, NR'R'', or SR''', where R═H, benzyl, trimethylsilyl, tert-butyldimethylsilyl, tert-butyldiphenylsilyl, or acetate group, R', R'' independently═H, alkyl, allyl, benzyl, tosylate group, C(═O)-alkyl, or C(═O)—Bn, R'''═H, alkyl, or acetate group, R[6] is H, CH$_3$, CH$_2$OH, CH$_2$-glycoside group, or CH$_2$—OGP in which GP is a protector group selected from alkyl, benzyl, trimethylsilyl, tert-butyldimethylsilyl, tert-butyldiphenylsilyl, or acetate group, R[7]═OH, OGP', NH$_2$, N$_3$, NHGP', or NGP'GP'' in which GP' and GP'' are independently selected from alkyl, benzyl, trimethylsilyl, tertbutyldimethylsilyl, tert-butyldiphenylsilyl, or acetate group, R[8] is a hydrogen atom H or a free or protected alcohol function, if R[2]═R[3]═H, CH$_3$, CH(CH$_3$)$_2$, CH$_2$CH(CH$_3$)$_2$, or CH(CH$_3$)CH$_2$CH$_3$ then R[1]═

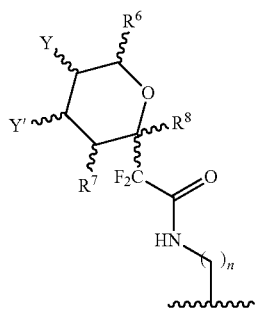

in which: n is an integer between 3 and 4,

Y, Y' are independent groups in which Y, Y'H, OR, N$_3$, NR'R'', or SR''', where R═H, benzyl, trimethylsilyl, tert-butyldimethylsilyl, tert-butyldiphenylsilyl, or acetate group, R', R'' independently═H, alkyl, allyl, benzyl, tosylate group, C(═O)-alkyl, or C(═O)—Bn, R'''═H, alkyl, or acetate group, R[6] is H, CH$_3$, CH$_2$OH, CH$_2$-glycoside group, or CH$_2$—OGP in which GP is a protector group selected from alkyl, benzyl, trimethylsilyl, tert-butyldimethylsilyl, tert-butyldiphenylsilyl, or acetate group, R[7]═OH, OGP', NH$_2$, N$_3$, NHGP', or NGP'GP'' in which GP' and GP'' are independently selected from alkyl, benzyl, trimethylsilyl, tertbutyldimethylsilyl, tert-butyldiphenylsilyl, or acetate group, R[8] is a hydrogen atom H or a free or protected alcohol function.

According to another embodiment, there is provided an in vitro method for protecting isolated neurosensory precursor cells from prostaglandin E2 toxicity comprising the step of:

a) contacting an isolated neurosensory precursor cells with a gem-difluorinated C-glycopeptide compound of general formula I, or a pharmaceutically acceptable base, addition salt with an acid, hydrate or solvate thereof, and then washing the isolated neurosensory cells to remove the compound:

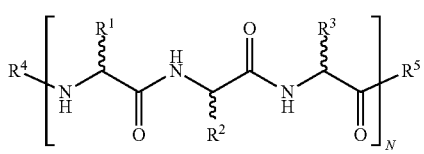

(I)

in which:

N is an integer between 1 and 5, $R^4$=H, $AA_1$, or $AA_1$-$AA_2$, $R^5$=OH, $AA_1$, or $AA_1$-$AA_2$, $AA_1$ and $AA_2$ independently represent amino acids with a non-polar side chain and $R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

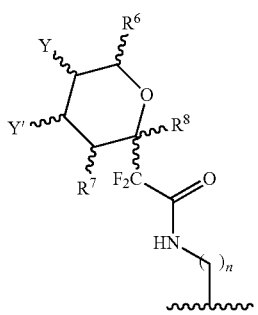

in which:

n is an integer between 3 and 4,

Y, Y' are independent groups in which Y, Y'=H, OR, $N_3$, NR'R", or SR''', where R=H, benzyl, trimethylsilyl, tert-butyldimethylsilyl, tert-butyldiphenylsilyl or acetate group, R', R" independently=H, alkyl, allyl, benzyl, tosylate group, C(=O)-alkyl or C(=O)—Bn, R'''=H, alkyl, or acetate group, $R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP' or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, and if $R^1$=$R^2$=H, $CH_3$, $CH_2Ph$, $CH(CH_3)_2$, $CH_2CH(CH_3)_2$, or $CH(CH_3)CH_2CH_3$ then $R^3$=

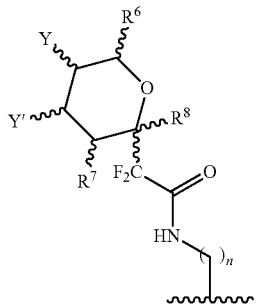

in which: n is an integer between 3 and 4,

Y, Y' are independent groups in which Y, Y'=H, OR, $N_3$, NR'R", or SR''', where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'''=H, alkyl, or acetate group, $R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group, $R^8$ is a hydrogen atom H or a free or protected alcohol function, if $R^1$=$R^3$=H, $CH_3$, $CH_2Ph$, $CH(CH_3)_2$, $CH_2CH(CH_3)_2$, or $CH(CH_3)CH_2CH_3$ then $R^2$=

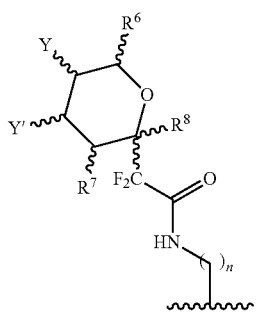

in which: n is an integer between 3 and 4,

Y, Y' are independent groups in which Y, Y'=H, OR, $N_3$, NR'R", or SR''', where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'''=H, alkyl, or acetate group, $R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group, $R^8$ is a hydrogen atom H or a free or protected alcohol function, if $R^2$=$R^3$=H, $CH_3$, $CH(CH_3)_2$, $CH_2CH(CH_3)_2$, or $CH(CH_3)CH_2CH_3$ then $R^1$=

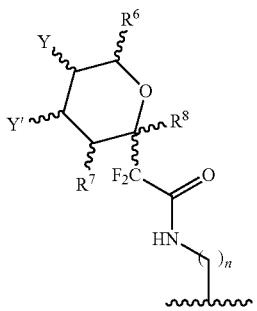

in which: n is an integer between 3 and 4,

Y, Y' are independent groups in which Y, Y'H, OR, $N_3$, NR'R", or SR'", where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'"=H, alkyl, or acetate group, $R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group, $R^8$ is a hydrogen atom H or a free or protected alcohol function wherein the compound protects the isolated neurosensory precursor cells from prostaglandin E2 toxicity.

The contacting may be prior to a transplantation in a subject in need thereof.

The compound of formula I may be a compound of formula II:

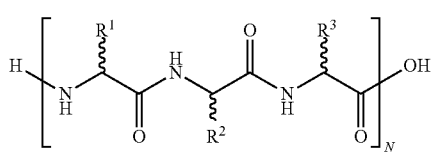

(II)

in which: N is an integer between 1 and 5, and $R^1$, $R^2$, $R^3$ are independent groups in which two of $R^1$, $R^2$ and $R^3$ are selected from H, $CH_3$ and the remaining $R^1$, $R^2$ and $R^3$ is

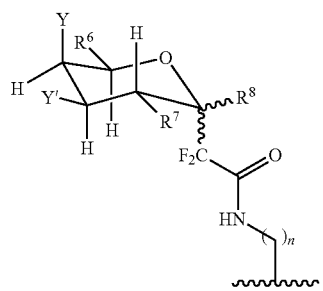

in which: n is an integer between 3 and 4,

Y, Y' are independent groups in which Y, Y'=H, OR, $N_3$, NR'R" or SR'", where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'"=H, alkyl, or acetate group, $R^6$ is selected from H, $CH_3$, $CH_2OH$, $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', NGP'GP" in which GP' and GP" are independently selected from alkyl, benzyl, trimethylsilyl, tert-butyldimethylsilyl, tert-butyldiphenylsilyl or acetate group, $R^8$ is a hydrogen atom H or a free or protected alcohol function, and if $R^1$=$R^2$=H or $CH_3$, then $R^3$=

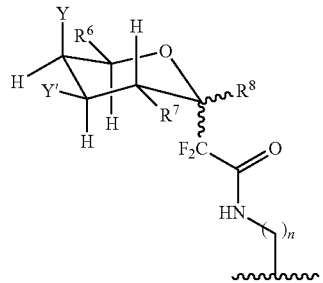

in which: n is an integer between 3 and 4,

Y, Y' are independent groups in which Y, Y'=H, OR, $N_3$, NR'R", or SR'", where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'"=H, alkyl, or acetate group, $R^6$ is selected from H, $CH_3$, $CH_2OH$, $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', NGP'GP" in which GP' and GP" are independently selected from alkyl, benzyl, trimethylsilyl, tert-butyldimethylsilyl, tert-butyldiphenylsilyl, or acetate group, R⁸ is a hydrogen atom H or a free or protected alcohol function,
if R¹=R³=H or CH₃,
then R²=

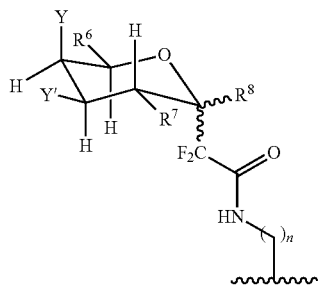

in which: n is an integer between 3 and 4,
Y, Y' are independent groups
in which Y, Y'=H, OR, N₃, NR'R'', SR''',
where R=H, benzyl, trimethylsilyl, tert-butyldimethylsilyl, tert-butyldiphenylsilyl, or acetate group,
R', R'' independently=H, alkyl, allyl,
Bn, tosylate, C(=O)-alkyl, or C(=O)—Bn,
R'''=H, alkyl, or acetate group,
R⁶ is selected from H, CH₃, CH₂OH, or CH₂—OGP in which GP is a protector group selected from alkyl, benzyl, trimethylsilyl, tert-butyldimethylsilyl, tert-butyldiphenylsilyl, or acetate group,
R⁷=OH, OGP', NH₂, N₃, NHGP', or NGP'GP'' in which GP' and GP'' are independently selected from alkyl, benzyl, trimethylsilyl, tert-butyldimethylsilyl, tert-butyldiphenylsilyl, or acetate group,
R⁸ is a hydrogen atom H or a free or protected alcohol function,
if R²=R³=H or CH₃,
then R¹=

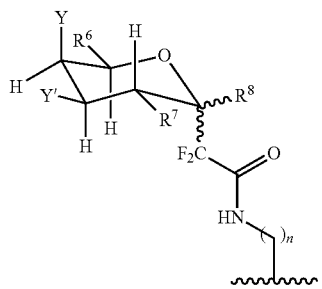

in which: n is an integer between 3 and 4,
Y, Y' are independent groups
in which Y, Y'H, OR, N₃, NR'R'', or SR''',
where R=H, benzyl, trimethylsilyl, tert-butyldimethylsilyl, tert-butyldiphenylsilyl, or acetate group,
R', R'' independently=H, alkyl, allyl, benzyl, tosylate group, C(=O)-alkyl, or C(=O)—Bn,
R'''=H, alkyl, or acetate group,
R⁶ is selected from H, CH₃, CH₂OH, or CH₂—OGP in which GP is a protector group selected from alkyl, benzyl, trimethylsilyl, tert-butyldimethylsilyl, tert-butyldiphenylsilyl, or acetate group,
R⁷=OH, OGP', NH₂, N₃, NHGP', or NGP'GP'' in which GP' and GP'' are independently selected from alkyl, benzyl, trimethylsilyl, tert-butyldimethylsilyl, tert-butyldiphenylsilyl, or acetate group,
R⁸ is a hydrogen atom or a free or protected alcohol function.

The compound of formula I may be a compound of formula III:

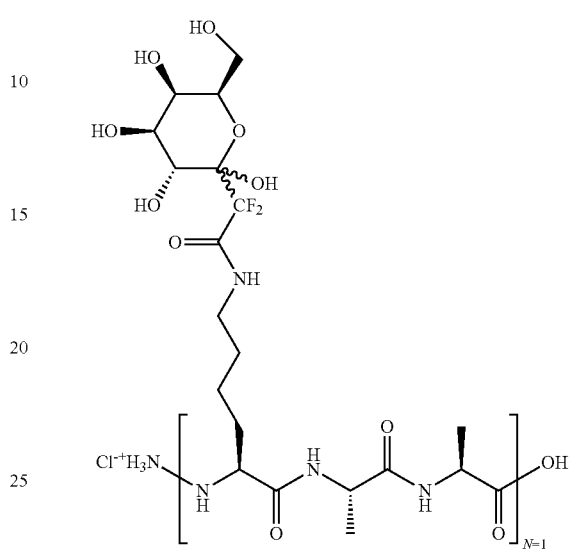

(III).

The isolated neurosensory precursor cell may be contacted with the compound for at least 1 hour.

The concentration of the compound may be from about 1 mg/ml to about 5 mg/ml.

The concentration of the compound may be from about 1 mg/ml to about 3 mg/ml, or from about 3 mg/ml to about 5 mg/ml.

The isolated neurosensory precursor cell may be a photoreceptor precursor cell.

According to another embodiment, there is provided an isolated neurosensory precursor cell prepared according to the method of the present invention.

According to another embodiment, there is provided a method of transplanting isolated neurosensory precursor cell in a subject in need thereof comprising the steps of
a) transplanting an isolated neurosensory precursor cell prepared according to the method of the present invention, in the subject in need thereof.

The method may further comprise the step of:
b) transplanting the treated isolated neurosensory precursor cell from step a) in the subject in need thereof, wherein the subject may be receiving an immunosuppressant drug.

The immunosuppressant drug may be daclizumab, sirolimus, tacrolimus, cyclosporine, or a combination thereof.

The subject may be a human subject.

According to another embodiment, there is provided a method of treating a retinal degenerative disease comprising the step of:
a) transplanting an isolated neurosensory precursor cell prepared according to the method of the present invention in the subject in need thereof.

The retinal degenerative disease may be age-related macular degeneration (AMD), retinitis pigmentosa (RP), retinal vasculitis, or sarcoidosis.

According to another embodiment, there is provided a use of an isolated neurosensory precursor cell prepared according to the method of the present invention, for transplantation to a subject in need thereof.

According to another embodiment, there is provided a use of an isolated neurosensory precursor cell prepared according to the method of the present invention, for treatment of a retinal degenerative disease in a subject in need thereof.

The retinal degenerative disease may be age-related macular degeneration (AMD), retinitis pigmentosa (RP), retinal vasculitis, or sarcoidosis.

According to another embodiment, there is provided an isolated neurosensory precursor cell according to the method of the present invention, for transplantation to a subject in need thereof.

The isolated neurosensory precursor cell may be a photoreceptor precursor cell.

According to another embodiment, there is provided an isolated neurosensory precursor cell contacted with a gem-difluorinated C-glycopeptide compound of general formula I, or a pharmaceutically acceptable base, addition salt with an acid, hydrate or solvate thereof:

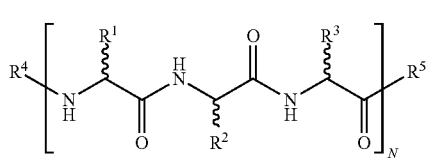

in which:
N is an integer between 1 and 5,
$R^4$=H, $AA_1$, or $AA_1$-$AA_2$,
$R^5$=OH, $AA_1$, or $AA_1$-$AA_2$,
$AA_1$ and $AA_2$ independently represent amino acids with a non-polar side chain
and
$R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

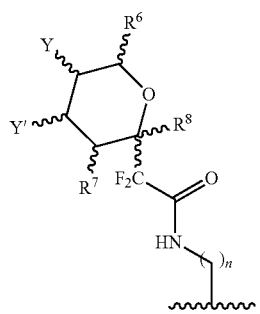

in which:
n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl or acetate group,
R', R" independently=H, alkyl, allyl, benzyl, tosylate group, C(=O)-alkyl or C(=O)—Bn,
R'''=H, alkyl, or acetate group,
$R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP' or NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
and
if $R^1$=$R^2$=H, $CH_3$, $CH_2Ph$, $CH(CH_3)_2$, $CH_2CH(CH_3)_2$, or $CH(CH_3)CH_2CH_3$
then $R^3$=

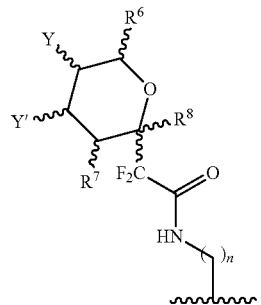

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function,
if $R^1$=$R^3$=H, $CH_3$, $CH_2Ph$, $CH(CH_3)_2$, $CH_2CH(CH_3)_2$, or $CH(CH_3)CH_2CH_3$
then $R^2$=

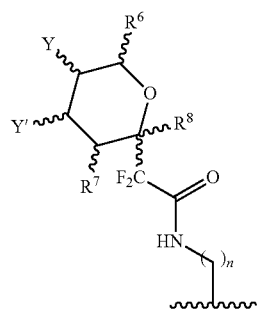

in which: n is an integer between 3 and 4,

Y, Y' are independent groups
in which Y, Y'=H, OR, N₃, NR'R", or SR'",
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'"=H, alkyl, or acetate group,
R⁶ is H, CH₃, CH₂OH, CH₂-glycoside group, or CH₂OGP in which GP is a protector group selected from alkyl, benzyl, trimethylsilyl, tert-butyldimethylsilyl, tert-butyldiphenylsilyl, or acetate group,
R⁷=OH, OGP', NH₂, N₃, NHGP', or NGP'GP" in which GP' and GP" are independently selected from alkyl, benzyl, trimethylsilyl, tertbutyldimethylsilyl, tert-butyldiphenylsilyl, or acetate group,
R⁸ is a hydrogen atom H or a free or protected alcohol function, if R²=R³=H, CH₃, CH(CH₃)₂, CH₂CH(CH₃)₂, or CH(CH₃)CH₂CH₃
then R¹=

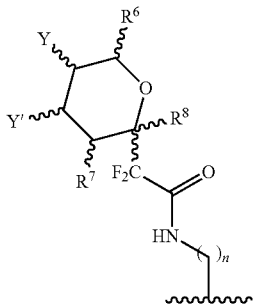

in which: n is an integer between 3 and 4,
Y, Y' are independent groups
in which Y, Y'H, OR, N₃, NR'R", or SR'",
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'"=H, alkyl, or acetate group,
R⁶ is H, CH₃, CH₂OH, CH₂-glycoside group, or CH₂—OGP in which GP is a protector group selected from alkyl, benzyl, trimethylsilyl, tert-butyldimethylsilyl, tert-butyldiphenylsilyl, or acetate group,
R⁷=OH, OGP', NH₂, N₃, NHGP', or NGP'GP" in which GP' and GP" are independently selected from alkyl, benzyl, trimethylsilyl, tertbutyldimethylsilyl, tert-butyldiphenylsilyl, or acetate group,
R⁸ is a hydrogen atom H or a free or protected alcohol function.

The compound of formula I may be a compound of formula II:

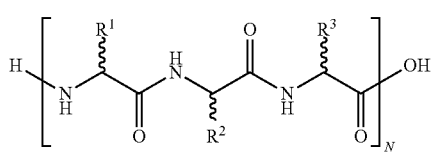

(II)

in which: N is an integer between 1 and 5,
and

R¹, R², R³ are independent groups in which two of R¹, R² and R³ are selected from H, CH₃ and the remaining R¹, R² and R³ is

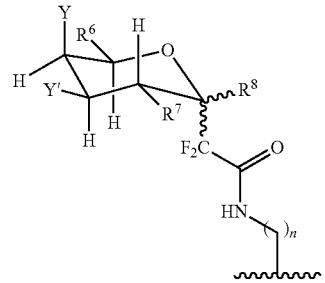

in which: n is an integer between 3 and 4,
Y, Y' are independent groups
in which Y, Y'=H, OR, N₃, NR'R" or SR'",
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)alkyl, or C(=O)—Bn,
R'"=H, alkyl, or acetate group,
R⁶ is selected from H, CH₃, CH₂OH, CH₂—OGP in which GP is a protector group selected from alkyl, benzyl, trimethylsilyl, tert-butyldimethylsilyl, tert-butyldiphenylsilyl, or acetate group,
R⁷=OH, OGP', NH₂, N₃, NHGP', NGP'GP" in which GP' and GP" are independently selected from alkyl, benzyl, trimethylsilyl, tert-butyldimethylsilyl, tert-butyldiphenylsilyl or acetate group,
R⁸ is a hydrogen atom H or a free or protected alcohol function, and
if R¹=R²=H or CH₃,
then R³=

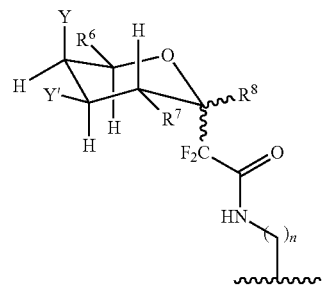

in which: n is an integer between 3 and 4,
Y, Y' are independent groups
in which Y, Y'=H, OR, N₃, NR'R", or SR'",
where R=H, benzyl, trimethylsilyl, tert-butyldimethylsilyl, tert-butyldiphenylsilyl, or acetate group,
R', R" independently=H, alkyl, allyl, benzyl, tosylate group,
C(=O)-alkyl, or
C(=O)—Bn,
R'"=H, alkyl, or acetate group,
R⁶ is selected from H, CH₃, CH₂OH, CH₂—OGP in which GP is a protector group selected from alkyl, benzyl, trimethylsilyl, tert-butyldimethylsilyl, tert-butyldiphenylsilyl, or acetate group, $R^7$=OH, OGP', NH$_2$, N$_3$, NHGP', NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, if $R^1$=$R^3$=H or CH$_3$, then $R^2$=

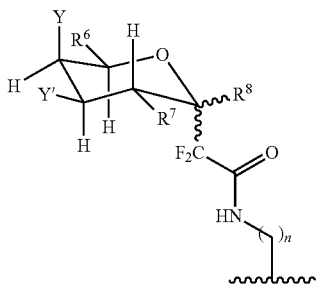

in which: n is an integer between 3 and 4,

Y, Y' are independent groups in which Y, Y'=H, OR, N$_3$, NR'R", SR''', where R=H, benzyl, trimethylsilyl, tert-butyldimethylsilyl, tert-butyldiphenylsilyl, or acetate group, R', R" independently=H, alkyl, allyl, Bn, tosylate, C(=O)-alkyl, or C(=O)—Bn, R'''=H, alkyl, or acetate group, $R^6$ is selected from H, CH$_3$, CH$_2$OH, or CH$_2$—OGP in which GP is a protector group selected from alkyl, benzyl, trimethylsilyl, tert-butyldimethylsilyl, tert-butyldiphenylsilyl, or acetate group, $R^7$=OH, OGP', NH$_2$, N$_3$, NHGP', or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, if $R^2$=$R^3$=H or CH$_3$, then $R^1$=

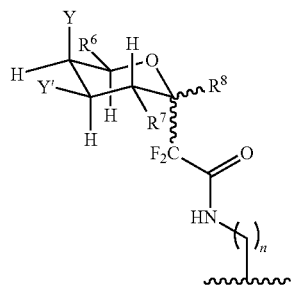

in which: n is an integer between 3 and 4,

Y, Y' are independent groups in which Y, Y'H, OR, N$_3$, NR'R", or SR''', where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'''=H, alkyl, or acetate group, $R^6$ is selected from H, CH$_3$, CH$_2$OH, or CH$_2$—OGP in which GP is a protector group selected from alkyl, benzyl, trimethylsilyl, tert-butyldimethylsilyl, tert-butyldiphenylsilyl, or acetate group, $R^7$=OH, OGP', NH$_2$, N$_3$, NHGP', or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom or a free or protected alcohol function.

The compound of formula I may be a compound of formula III:

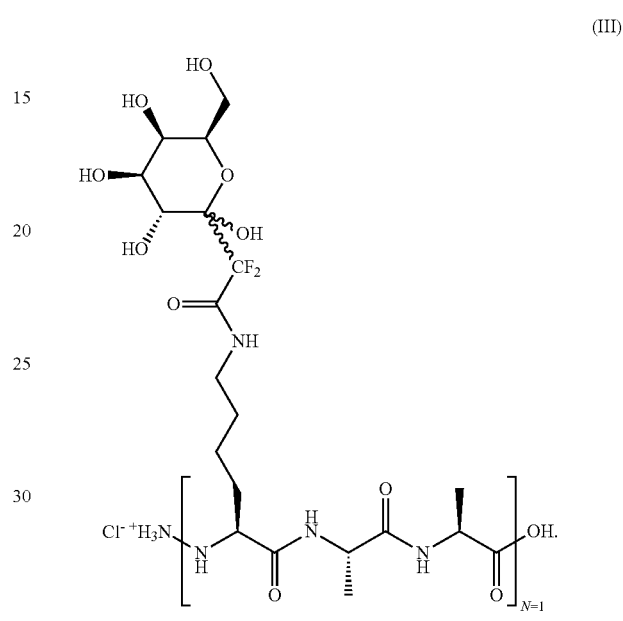

(III)

The isolated neurosensory precursor cell may be contacted with from about from about 0.01 mg/ml to about 5 mg/ml of the compound of formula I, formula II or formula III.

The isolated neurosensory precursor cell may be contacted with from about from about 1 mg/ml to about 5 mg/ml, or from about 1 mg/ml to about 3 mg/ml, or from about 3 mg/ml to about 5 mg/ml of the compound of formula I, formula II or formula III.

The isolated neurosensory precursor cell may be contacted with the compound for at least 1 hour.

The isolated neurosensory precursor cell may be washed to remove the compound of formula I, II or III.

The isolated neurosensory precursor cell may be a photoreceptor precursor cell.

According to another embodiment, there may be provided a use of a gem-difluorinated C-glycopeptide compound of general formula I, or a pharmaceutically acceptable base, addition salt with an acid, hydrate or solvate thereof, for enhancing engraftment of isolated neurosensory precursor cell in a subject in need thereof:

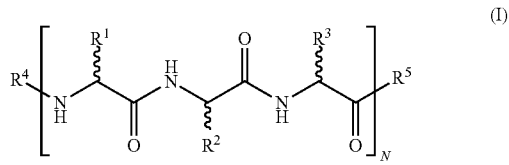

(I)

in which:
N is an integer between 1 and 5,
$R^4$=H, $AA_1$, or $AA_1$-$AA_2$,
$R^5$=OH, $AA_1$, or $AA_1$-$AA_2$,
$AA_1$ and $AA_2$ independently represent amino acids with a non-polar side chain
and
$R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

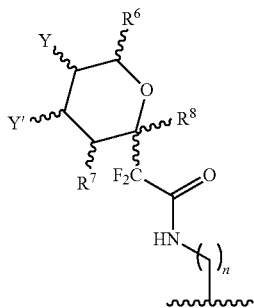

in which:
n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl or acetate group,
R', R" independently=H, alkyl, allyl, benzyl, tosylate group, C(=O)-alkyl or C(=O)—Bn,
R'''=H, alkyl, or acetate group,
$R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP' or NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
and
if $R^1$=$R^2$=H, $CH_3$, $CH_2Ph$, $CH(CH_3)_2$, $CH_2CH(CH_3)_2$, or $CH(CH_3)CH_2CH_3$
then $R^3$=

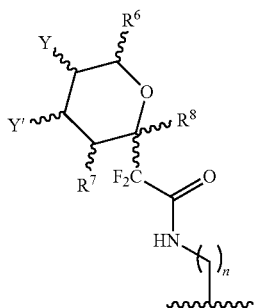

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function,
if $R^1$=$R^3$=H, $CH_3$, $CH_2Ph$, $CH(CH_3)_2$, $CH_2CH(CH_3)_2$, or $CH(CH_3)CH_2CH_3$
then $R^2$=

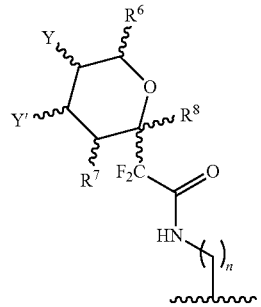

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function, if $R^2=R^3=H$, $CH_3$, $CH(CH_3)_2$, $CH_2CH(CH_3)_2$, or $CH(CH_3)CH_2CH_3$
then $R^1=$

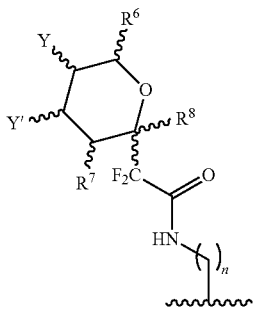

in which: n is an integer between 3 and 4,
Y, Y' are independent groups
in which Y, Y'=H, OR, $N_3$, NR'R", or SR'",
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'"=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function.

According to another embodiment, there is provided an use of a gem-difluorinated C-glycopeptide compound of general formula I, or a pharmaceutically acceptable base, addition salt with an acid, hydrate or solvate thereof, for protecting isolated neurosensory precursor cell from prostaglandin E2 toxicity prior to transplantation in a subject in need thereof:

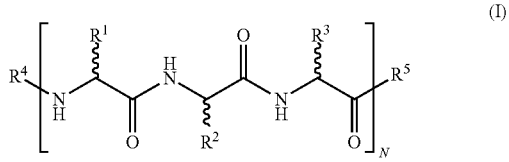

(I)

in which:
N is an integer between 1 and 5,
$R^4$=H, $AA_1$, or $AA_1$-$AA_2$,
$R^5$=OH, $AA_1$, or $AA_1$-$AA_2$,
$AA_1$ and $AA_2$ independently represent amino acids with a non-polar side chain
and
$R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

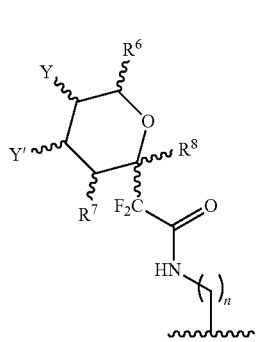

in which:
n is an integer between 3 and 4,
Y, Y' are independent groups
in which Y, Y'=H, OR, $N_3$, NR'R", or SR'",
where R=H, benzyl, trimethylsilyl, tert-butyldimethylsilyl, tert-butyldiphenylsilyl or acetate group,
R', R" independently=H, alkyl, allyl, benzyl, tosylate group, C(=O)-alkyl or C(=O)—Bn,
R'"=H, alkyl, or acetate group,
$R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP' or NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
and
if $R^1=R^2=H$, $CH_3$, $CH_2Ph$, $CH(CH_3)_2$, $CH_2CH(CH_3)_2$, or $CH(CH_3)CH_2CH_3$
then $R^3=$

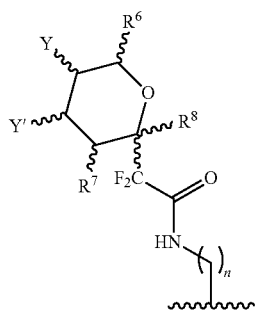

in which: n is an integer between 3 and 4,
Y, Y' are independent groups
in which Y, Y'=H, OR, $N_3$, NR'R", or SR'",
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'"=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group, $R^8$ is a hydrogen atom H or a free or protected alcohol function, if $R^1 = R^3 = H$, $CH_3$, $CH_2Ph$, $CH(CH_3)_2$, $CH_2CH(CH_3)_2$, or $CH(CH_3)CH_2CH_3$ then $R^2=$

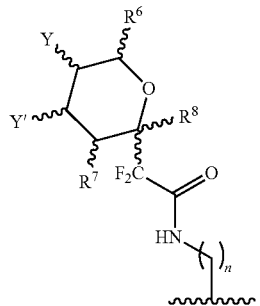

in which: n is an integer between 3 and 4,

Y, Y' are independent groups
  in which Y, Y'=H, OR, $N_3$, NR'R", or SR''',
    where R=H, benzyl, trimethylsilyl, tert-butyldimethylsilyl, tert-butyldiphenylsilyl, or acetate group,
    R', R" independently=H, alkyl, allyl, benzyl, tosylate group, C(=O)-alkyl, or C(=O)—Bn,
    R'''=H, alkyl, or acetate group, $R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group, $R^7=$OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group, $R^8$ is a hydrogen atom H or a free or protected alcohol function, if $R^2 = R^3 = H$, $CH_3$, $CH(CH_3)_2$, $CH_2CH(CH_3)_2$, or $CH(CH_3)CH_2CH_3$ then $R^1=$

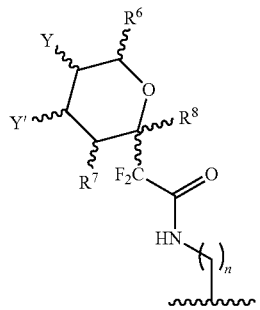

in which: n is an integer between 3 and 4,
Y, Y' are independent groups
  in which Y, Y'H, OR, $N_3$, NR'R", or SR''',
    where R=H, benzyl, trimethylsilyl, tert-butyldimethylsilyl, tert-butyldiphenylsilyl, or acetate group,
    R', R" independently=H, alkyl, allyl, benzyl, tosylate group, C(=O)-alkyl, or C(=O)—Bn,
    R'''=H, alkyl, or acetate group, $R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group, $R^7=$OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group, $R^8$ is a hydrogen atom H or a free or protected alcohol function.

The subject may be a human subject.

The isolated neurosensory precursor cell may be a photoreceptor precursor cell.

The compound of formula I may be a compound of formula II:

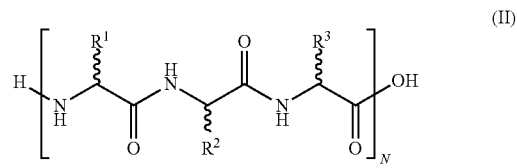

in which: N is an integer between 1 and 5,
and $R^1$, $R^2$, $R^3$ are independent groups in which two of $R^1$, $R^2$ and $R^3$ are selected from H, $CH_3$ and the remaining $R^1$, $R^2$ and $R^3$ is

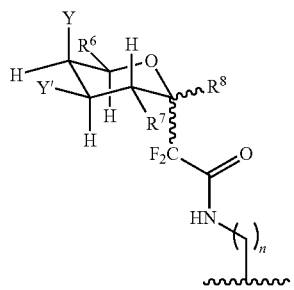

in which: n is an integer between 3 and 4,
Y, Y' are independent groups
  in which Y, Y'=H, OR, $N_3$, NR'R" or SR''',
    where R=H, benzyl, trimethylsilyl, tert-butyldimethylsilyl, tert-butyldiphenylsilyl, or acetate group,
    R', R" independently=H, alkyl, allyl, benzyl, tosylate group, C(=O)-alkyl, or C(=O)—Bn,
    R'''=H, alkyl, or acetate group, $R^6$ is selected from H, $CH_3$, $CH_2OH$, $CH_2$—OGP in which GP is a protector group selected from alkyl, benzyl, trimethylsilyl, tert-butyldimethylsilyl, tert-butyldiphenylsilyl, or acetate group, $R^7=$OH, OGP', $NH_2$, $N_3$, NHGP', NGP'GP" in which GP' and GP" are independently selected from alkyl, benzyl, trimethylsilyl, tert-butyldimethylsilyl, tert-butyldiphenylsilyl or acetate group, $R^8$ is a hydrogen atom H or a free or protected alcohol function, and
if $R^1=R^2=$H or $CH_3$,
then $R^3=$

[structure: cyclohexane ring with substituents Y, $R^6$, H, H, Y', H, O, $R^8$, $R^7$, $F_2C$—C(=O)—NH—(CH$_2$)$_n$—]

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group,
C(=O)-alkyl, or
C(=O)—Bn,
R'''=H, alkyl, or acetate group,
$R^6$ is selected from H, $CH_3$, $CH_2OH$, $CH_2$—OGP in which GP is a protector group selected from alkyl, benzyl, trimethylsilyl, tert-butyldimethylsilyl, tert-butyldiphenylsilyl, or acetate group,
$R^7=$OH, OGP', $NH_2$, $N_3$, NHGP', NGP'GP'' in which GP' and GP'' are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
if $R^1=R^3=$H or $CH_3$,
then $R^2=$

[structure similar to above]

in which: n is an integer between 3 and 4,
Y, Y' are independent groups
in which Y, Y'=H, OR, $N_3$, NR'R", SR''',
where R=H, benzyl, trimethylsilyl, tert-butyldimethylsilyl, tert-butyldiphenylsilyl, or acetate group,
R', R" independently=H, alkyl, allyl, Bn, tosylate, C(=O)-alkyl, or C(=O)—Bn,
R'''=H, alkyl, or acetate group,
$R^6$ is selected from H, $CH_3$, $CH_2OH$, or $CH_2$—OGP in which GP is a protector group selected from alkyl, benzyl, trimethylsilyl, tert-butyldimethylsilyl, tert-butyldiphenylsilyl, or acetate group,
$R^7=$OH, OGP', $NH_2$, $N_3$, NHGP', or NGP'GP'' in which GP' and GP'' are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
if $R^2=R^3=$H or $CH_3$,
then $R^1=$

[structure similar to above]

in which: n is an integer between 3 and 4,
Y, Y' are independent groups
in which Y, Y'H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is selected from H, $CH_3$, $CH_2OH$, or $CH_2$—OGP in which GP is a protector group selected from alkyl, benzyl, trimethylsilyl, tert-butyldimethylsilyl, tert-butyldiphenylsilyl, or acetate group,
$R^7=$OH, OGP', $NH_2$, $N_3$, NHGP', or NGP'GP'' in which GP' and GP'' are independently selected from alkyl, benzyl, trimethylsilyl, tert-butyldimethylsilyl, tert-butyldiphenylsilyl, or acetate group,
$R^8$ is a hydrogen atom or a free or protected alcohol function.
The compound of formula I may be a compound of formula III:

(III)

[structure: sugar moiety (HO, HO, HO, HO, O, OH) linked via $CF_2$—C(=O)—NH— to lysine-containing peptide chain with Cl$^-$ $^+H_3N$—, repeating amide units, ending —OH, with N=1]

The isolated neurosensory precursor cell may be contacted with from about from about 0.01 mg/ml to about 5 mg/ml of the compound of formula I, formula II or formula III.

The isolated neurosensory precursor cell may be contacted with from about from about 1 mg/ml to about 5 mg/ml, or from about 1 mg/ml to about 3 mg/ml, or from about 3 mg/ml to about 5 mg/ml of the compound of formula I, formula II or formula III.

The isolated neurosensory precursor cell may be contacted with the compound for at least 1 hour.

The isolated neurosensory precursor cell may be washed to remove the compound of formula I, II or III.

The isolated neurosensory precursor cell may be a photoreceptor precursor cell.

The use may be for the treatment of a retinal degenerative disease in a subject in need thereof.

The retinal degenerative disease may be age-related macular degeneration (AMD), retinitis pigmentosa (RP), retinal vasculitis, or sarcoidosis.

According to another embodiment, there is provided an gem-difluorinated C-glycopeptide compound of general formula I, or a pharmaceutically acceptable base, addition salt with an acid, hydrate or solvate thereof, for use in enhancing engraftment of an isolated neurosensory precursor cell in a subject in need thereof:

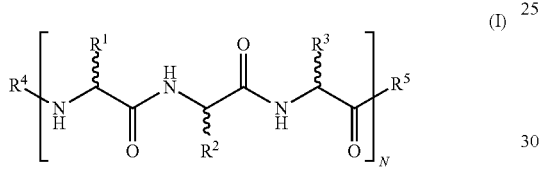

in which:
N is an integer between 1 and 5,
$R^4$=H, $AA_1$, or $AA_1$-$AA_2$,
$R^5$=OH, $AA_1$, or $AA_1$-$AA_2$,
$AA_1$ and $AA_2$ independently represent amino acids with a non-polar side chain and
$R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

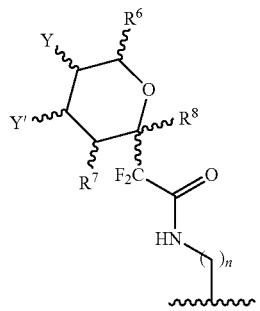

in which:
n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl or acetate group,
R', R" independently=H, alkyl, allyl, benzyl, tosylate group, C(=O)-alkyl or C(=O)—Bn,
R'''=H, alkyl, or acetate group,
$R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP' or NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
and
if $R^1$=$R^2$=H, $CH_3$, $CH_2Ph$, $CH(CH_3)_2$, $CH_2CH(CH_3)_2$, or $CH(CH_3)CH_2CH_3$
then $R^3$=

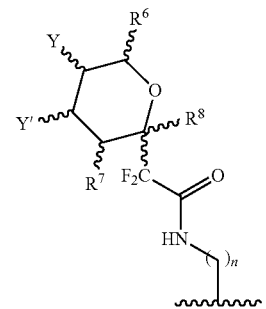

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function,
if $R^1$=$R^3$=H, $CH_3$, $CH_2Ph$, $CH(CH_3)_2$, $CH_2CH(CH_3)_2$, or $CH(CH_3)CH_2CH_3$
then $R^2$=

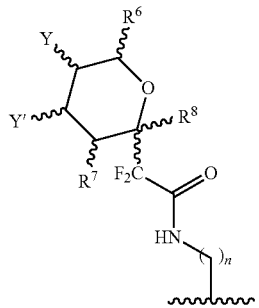

in which: n is an integer between 3 and 4,

Y, Y' are independent groups
in which Y, Y'=H, OR, $N_3$. NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function,
if $R^2=R^3$=H, $CH_3$, $CH(CH_3)_2$, $CH_2CH(CH_3)_2$, or $CH(CH_3)CH_2CH_3$
then $R^1$=

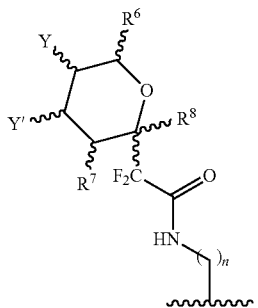

in which: n is an integer between 3 and 4,
Y, Y' are independent groups
in which Y, Y'H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function.

According to another embodiment, there is provided an gem-difluorinated C-glycopeptide compound of general formula I, or a pharmaceutically acceptable base, addition salt with an acid, hydrate or solvate thereof, for protecting isolated neurosensory precursor cell from prostaglandin E2 toxicity prior to transplantation in a subject in need thereof:

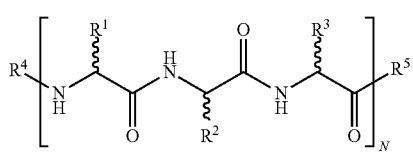

(I)

in which:
N is an integer between 1 and 5,
$R^4$=H, $AA_1$, or $AA_1$-$AA_2$,
$R^5$=OH, $AA_1$, or $AA_1$-$AA_2$,
$AA_1$ and $AA_2$ independently represent amino acids with a non-polar side chain
and
$R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

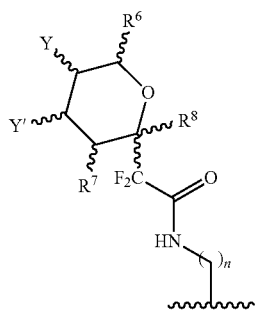

in which:
n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl or acetate group,
R', R" independently=H, alkyl, allyl, benzyl, tosylate group, C(=O)-alkyl or C(=O)—Bn,
R'''=H, alkyl, or acetate group,
$R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP' or NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
and
if $R^1=R^2$=H, $CH_3$, $CH_2Ph$, $CH(CH_3)_2$, $CH_2CH(CH_3)_2$, or $CH(CH_3)CH_2CH_3$
then $R^3$=

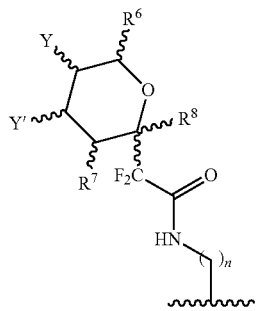

in which: n is an integer between 3 and 4,

Y, Y' are independent groups
  in which Y, Y'=H, OR, $N_3$, NR'R", or SR''',
    where R=H, benzyl, trimethylsilyl, tert-butyldimethylsilyl, tert-butyldiphenylsilyl, or acetate group,
    R', R" independently=H, alkyl, allyl, benzyl, tosylate group, C(=O)-alkyl, or C(=O)—Bn,
    R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function,
if $R^1=R^3$=H, $CH_3$, $CH_2Ph$, $CH(CH_3)_2$, $CH_2CH(CH_3)_2$, or $CH(CH_3)CH_2CH_3$
then $R^2$=

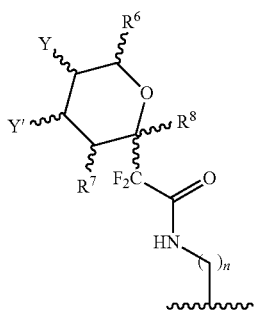

in which: n is an integer between 3 and 4,
Y, Y' are independent groups
  in which Y, Y'=H, OR, $N_3$, NR'R", or SR''',
    where R=H, benzyl, trimethylsilyl, tert-butyldimethylsilyl, tert-butyldiphenylsilyl, or acetate group,
    R', R" independently=H, alkyl, allyl, benzyl, tosylate group, C(=O)-alkyl, or C(=O)—Bn,
    R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function, if $R^2=R^3$=H, $CH_3$, $CH(CH_3)_2$, $CH_2CH(CH_3)_2$, or $CH(CH_3)CH_2CH_3$
then $R^1$=

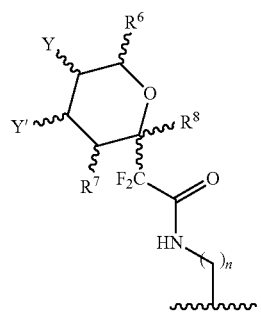

in which: n is an integer between 3 and 4,
Y, Y' are independent groups
  in which Y, Y'H, OR, $N_3$, NR'R", or SR''',
    where R=H, benzyl, trimethylsilyl, tert-butyldimethylsilyl, tert-butyldiphenylsilyl, or acetate group,
    R', R" independently=H, alkyl, allyl, benzyl, tosylate group, C(=O)-alkyl, or C(=O)—Bn,
    R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function.
The subject may be a human subject.
The compound of formula I may be a compound of formula II:

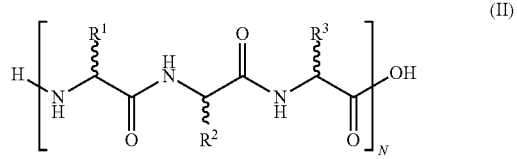

(II)

in which: N is an integer between 1 and 5,
and
$R^1$, $R^2$, $R^3$ are independent groups in which two of $R^1$, $R^2$ and $R^3$ are selected from H, $CH_3$ and the remaining $R^1$, $R^2$ and $R^3$ is

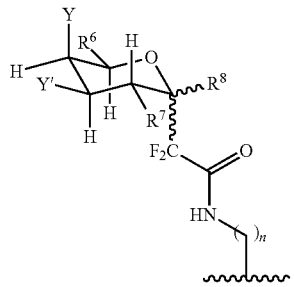

in which: n is an integer between 3 and 4,

Y, Y' are independent groups
in which Y, Y'=H, OR, $N_3$, NR'R" or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is selected from H, $CH_3$, $CH_2OH$, $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', NGP'GP" in which GP' and GP" are independently selected from alkyl, benzyl, trimethylsilyl, tert-butyldimethylsilyl, tert-butyldiphenylsilyl or acetate group,
$R^8$ is a hydrogen atom H or a free or protected alcohol function, and
if $R^1$=$R^2$=H or $CH_3$,
then $R^3$=

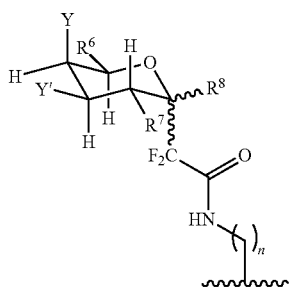

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or
C(=O)—Bn,
R'''=H, alkyl, or acetate group,
$R^6$ is selected from H, $CH_3$, $CH_2OH$, $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom H or a free or protected alcohol function, if $R^1$=$R^3$=H or $CH_3$,
then $R^2$=

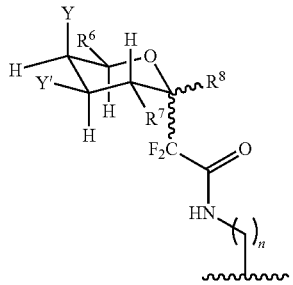

in which: n is an integer between 3 and 4,
Y, Y' are independent groups
in which Y, Y'=H, OR, $N_3$, NR'R", SR''',
where R=H, benzyl, trimethylsilyl, tert-butyldimethylsilyl, tert-butyldiphenylsilyl, or acetate group,
R', R" independently=H, alkyl, allyl,
Bn, tosylate, C(=O)-alkyl, or C(=O)—Bn,
R'''=H, alkyl, or acetate group,
$R^6$ is selected from H, $CH_3$, $CH_2OH$, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
if $R^2$=$R^3$=H or $CH_3$,
then $R^1$=

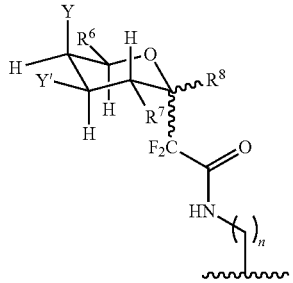

in which: n is an integer between 3 and 4,
Y, Y' are independent groups
in which Y, Y'H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is selected from H, $CH_3$, $CH_2OH$, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom or a free or protected alcohol function.

The compound of formula I may be a compound of formula III:

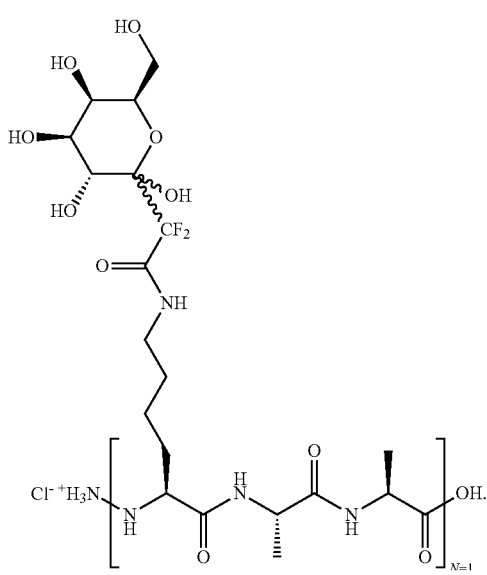

(III)

The contacting the isolated neurosensory precursor cells may be with from about from about 0.01 mg/ml to about 5 mg/ml, or from about 1 mg/ml to about 3 mg/ml, or from about 3 mg/ml to about 5 mg/ml of the compound of formula I, formula II or formula III.

The compound of formula I, II or III may be washed away to be remove from the isolated neurosensory precursor cell.

The compound of formula I, II or III may be in contact with the isolated neurosensory precursor cell may be contacted for at least 1 hour. The following terms are defined below.

The isolated neurosensory precursor cell may be a photoreceptor precursor cell.

The term «composition» as used herein is intended to encompass a product comprising the specified ingredients in the specified amounts, as well as any product which results, directly or indirectly, from combination of the specified ingredients in the specified amounts. Such term in relation to pharmaceutical composition or other compositions in general, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions or other compositions in general of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

The terms "neurosensory precursor cell", are intended to mean cells derived from human embryonic stem cells or induced pluripotent stem cells, isolated through known protocols and/or as described herein below, as well as cells of grown in vivo, ex vivo and/or in vitro.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from C3-10, the term alkyl also includes cycloalkyl groups, and combinations of linear or branched alkyl chains combined with cycloalkyl structures. When no number of carbon atoms is specified, C1-6 is intended.

"Cycloalkyl" is a subset of alkyl and means a saturated carbocyclic ring having a specified number of carbon atoms. Examples of cydoalkyl include cyclopropyl, cyclobutyl, cyclopentyl, cydohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., C1-6 alkoxy), or any number within this range [i.e., methoxy (MeO—), ethoxy, isopropoxy, etc.].

The term "alkylthio" refers to straight or branched chain alkylsulfides of the number of carbon atoms specified (e.g., C1-6 alkylthio), or any number within this range [i.e., methylthio (MeS—), ethylthio, isopropylthio, etc.].

The term "alkylamino" refers to straight or branched alkylamines of the number of carbon atoms specified (e.g., C1-6 alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., C1-6 alkylsulfonyl), or any number within this range [i.e., methylsulfonyl (MeSO$_2^-$), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO$^-$), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, 2-oxopiperidin-1-yl, 2-oxopyrrolidin-1-yl, 2-oxoazetidin-1-yl, 1,2,4-oxadiazin-5(6H)-one-3-yl, and the like.

"Heteroaryl" means an aromatic or partially aromatic heterocycle that contains at least one ring heteroatom selected from O, S and N. Heteroaryls thus include heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

Before describing the present invention in detail, a number of terms will be defined. As used herein, the singular forms "a", "an", and "the" include plural referents unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION OF THE PREFERRED EMBODIMENTS

Figure 1:
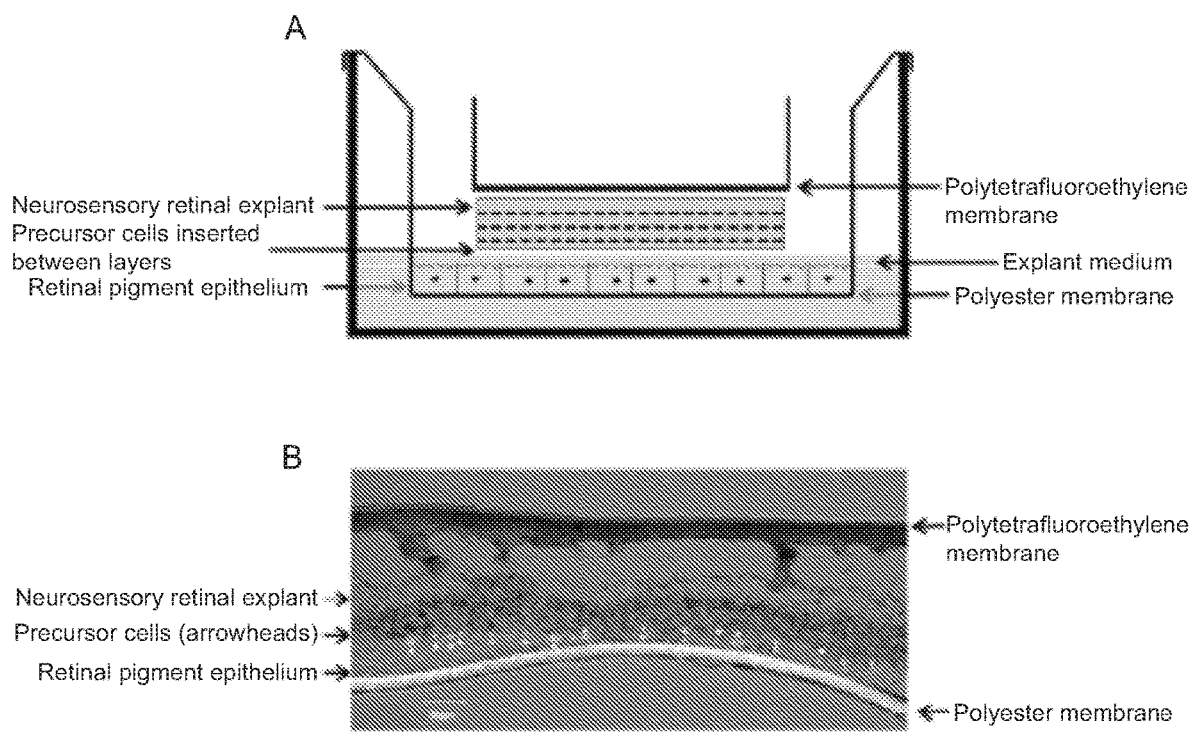
FIG. 1 illustrates the ex vivo model system as used to identify the present invention. (A) Schematic representation of the co-culture model system. Retinal pigment epithelium (RPE) is cultured on a polyester membrane and a neurosensory retinal explant is placed upon it with a tissue culture insert (polytetrafluoroethylene membrane). The photoreceptor layer faces the apical surface of the RPE. Precursor cells are placed upon the RPE surface before the retinal explant is added to the culture. (B) A low magnification representative image of a frozen cross-section through the co-culture model system. The precursor cells (arrowheads) reside on top of the RPE layer and underneath the retinal explant.

In embodiments there are disclosed an in vitro method for enhancing engraftment of neurosensory precursor cells comprising the step of:

a) contacting an isolated neurosensory precursor cell prior to a transplantation in a subject in need thereof, with a gem-difluorinated C-glycopeptide compound of general formula I, or a pharmaceutically acceptable base, addition salt with an acid, hydrate or solvate thereof, and then washing the isolated neurosensory precursor cells to remove the compound:

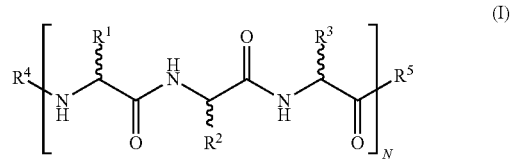

in which:

N is an integer between 1 and 5, $R^4$=H, $AA_1$, or $AA_1$-$AA_2$, $R^5$=OH, $AA_1$, or $AA_1$-$AA_2$, $AA_1$ and $AA_2$ independently represent amino acids with a non-polar side chain and $R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

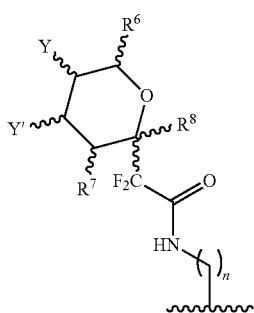

in which:
n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl or acetate group,
R', R" independently=H, alkyl, allyl, benzyl, tosylate group, C(=O)alkyl or C(=O)—Bn,
R'''=H, alkyl, or acetate group,
$R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP' or NGP'GP" in which GP' and GP" are independently selected from alkyl, benzyl, trimethylsilyl, tert-butyldimethylsilyl, tert-butyldiphenylsilyl, or acetate group,
$R^8$ is a hydrogen atom H or a free or protected alcohol function,
and
if $R^1$=$R^2$=H, $CH_3$, $CH_2Ph$, $CH(CH_3)_2$, $CH_2CH(CH_3)_2$, or $CH(CH_3)CH_2CH_3$
then $R^3$=

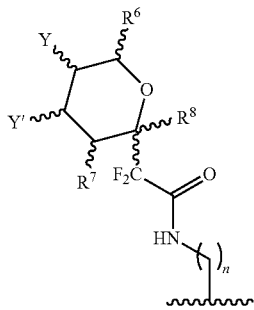

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group, $R^8$ is a hydrogen atom H or a free or protected alcohol function,
if $R^1$=$R^3$=H, $CH_3$, $CH_2Ph$, $CH(CH_3)_2$, $CH_2CH(CH_3)_2$, or $CH(CH_3)CH_2CH_3$
then $R^2$=

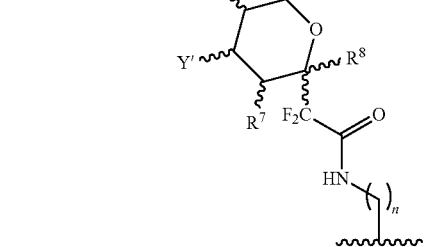

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function,
if $R^2$=$R^3$=H, $CH_3$, $CH(CH_3)_2$, $CH_2CH(CH_3)_2$, or $CH(CH_3)CH_2CH_3$
then $R^1$=

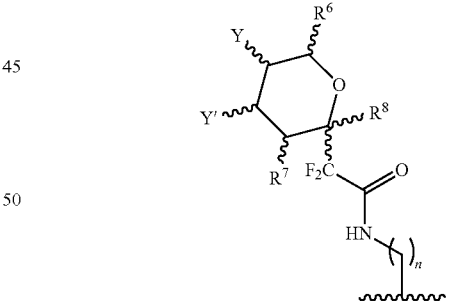

in which: n is an integer between 3 and 4,
Y, Y' are independent groups
in which Y, Y'H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group, $R^8$ is a hydrogen atom H or a free or protected alcohol function.

In another embodiments there is disclosed an in vitro method for protecting isolated neurosensory precursor cells from prostaglandin E2 toxicity comprising the step of:

a) contacting an isolated neurosensory precursor cells with a gem-difluorinated C-glycopeptide compound of general formula I, or a pharmaceutically acceptable base, addition salt with an acid, hydrate or solvate thereof, and then washing the isolated neurosensory cells to remove the compound:

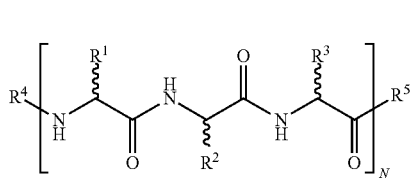
(I)

in which:
N is an integer between 1 and 5,
$R^4$=H, $AA_1$, or $AA_1$-$AA_2$,
$R^5$=OH, $AA_1$, or $AA_1$-$AA_2$,
$AA_1$ and $AA_2$ independently represent amino acids with a non-polar side chain
and
$R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

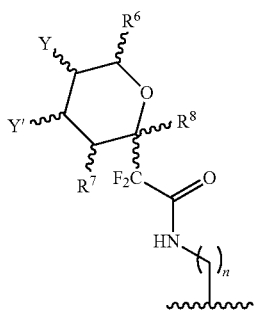

in which:
n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl or acetate group,
R', R" independently=H, alkyl, allyl, benzyl, tosylate group, C(=O)-alkyl or C(=O)—Bn,
R'''=H, alkyl, or acetate group,
$R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group,
$R^7$=OH, OGP', $NH_2$, $N_3$, NHGP' or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function,
and
if $R^1$=$R^2$=H, $CH_3$, $CH_2Ph$, $CH(CH_3)_2$, $CH_2CH(CH_3)_2$, or $CH(CH_3)CH_2CH_3$
then $R^3$=

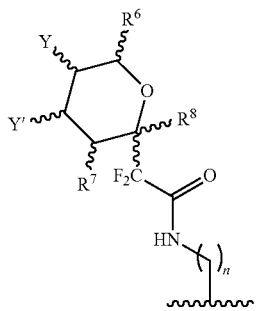

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group,
$R^7$=OH, OGP', $NH_2$, $N_3$, NHGP', or NGP'GP" in which GP' and GP" are independently selected from alkyl, benzyl, trimethylsilyl, tertbutyldimethylsilyl, tert-butyldiphenylsilyl, or acetate group,
$R^8$ is a hydrogen atom H or a free or protected alcohol function,
if $R^1$=$R^3$=H, $CH_3$, $CH_2Ph$, $CH(CH_3)_2$, $CH_2CH(CH_3)_2$, or $CH(CH_3)CH_2CH_3$
then $R^2$=

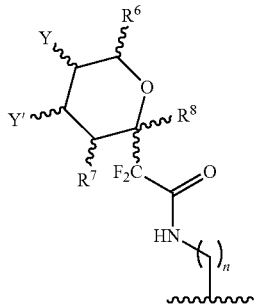

in which: n is an integer between 3 and 4,
Y, Y' are independent groups
in which Y, Y'=H, OR, $N_3$, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
$R^6$ is H, $CH_3$, $CH_2OH$, $CH_2$-glycoside group, or $CH_2$—OGP in which GP is a protector group selected from alkyl, benzyl, trimethylsilyl, tert-butyldimethylsilyl, tert-butyldiphenylsilyl, or acetate group, R⁷=OH, OGP', NH₂, N₃, NHGP', or NGP'GP" in which GP' and GP" are independently selected from alkyl, benzyl, trimethylsilyl, tertbutyldimethylsilyl, tert-butyldiphenylsilyl, or acetate group, R⁸ is a hydrogen atom H or a free or protected alcohol function, if R²=R³=H, CH₃, CH(CH₃)₂, CH₂CH(CH₃)₂, or CH(CH₃)CH₂CH₃ then R¹=

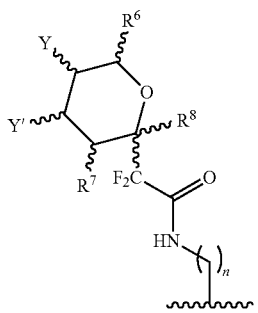

in which: n is an integer between 3 and 4,
Y, Y' are independent groups
in which Y, Y'H, OR, N₃, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
R⁶ is H, CH₃, CH₂OH, CH₂-glycoside group, or CH₂—OGP in which GP is a protector group selected from alkyl, benzyl, trimethylsilyl, tert-butyldimethylsilyl, tert-butyldiphenylsilyl, or acetate group,
R⁷=OH, OGP', NH₂, N₃, NHGP', or NGP'GP" in which GP' and GP" are independently selected from alkyl, benzyl, trimethylsilyl, tertbutyldimethylsilyl,
tert-butyldiphenylsilyl, or acetate group,
R⁸ is a hydrogen atom H or a free or protected alcohol function wherein the compound protects the isolated neurosensory precursor cells from prostaglandin E2 toxicity.

Contacting may be prior to a transplantation in a subject in need thereof, for example, a human subject.

In embodiments, the compound of formula I is a compound of formula II:

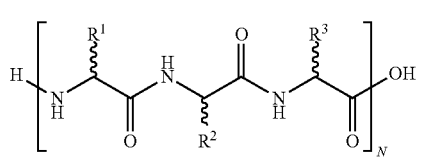

(II)

in which: N is an integer between 1 and 5,
and
R¹, R², R³ are independent groups in which two of R¹, R² and R³ are selected from H, CH₃ and the remaining R¹, R² and R³ is

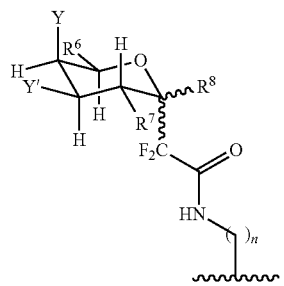

in which: n is an integer between 3 and 4,
Y, Y' are independent groups
in which Y, Y'=H, OR, N₃, NR'R" or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
R⁶ is selected from H, CH₃, CH₂OH, CH₂—OGP in which GP is a protector group selected from alkyl, benzyl, trimethylsilyl, tert-butyldimethylsilyl, tert-butyldiphenylsilyl, or acetate group,
R⁷=OH, OGP', NH₂, N₃, NHGP', NGP'GP" in which GP' and GP" are independently selected from alkyl, benzyl, trimethylsilyl, tert-butyldimethylsilyl, tert-butyldiphenylsilyl or acetate group,
R⁸ is a hydrogen atom H or a free or protected alcohol function,
and
if R¹=R²=H or CH₃,
then R³=

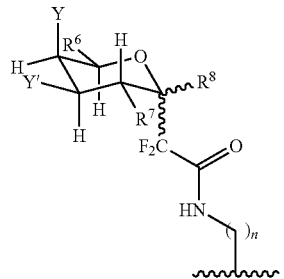

in which: n is an integer between 3 and 4,
Y, Y' are independent groups
in which Y, Y'=H, OR, N₃, NR'R", or SR''',
where R=H, benzyl, trimethylsilyl, tert-butyldimethylsilyl, tert-butyldiphenylsilyl, or acetate group,
R', R" independently=H, alkyl, allyl, benzyl, tosylate group, C(=O)-alkyl, or C(=O)—Bn,
R'''=H, alkyl, or acetate group,
R⁶ is selected from H, CH₃, CH₂OH, CH₂—OGP in which GP is a protector group selected from alkyl, benzyl, trimethylsilyl, tert-butyldimethylsilyl, tert-butyldiphenylsilyl, or acetate group,
R⁷=OH, OGP', NH₂, N₃, NHGP', NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, if $R^1=R^3=H$ or $CH_3$, then $R^2=$

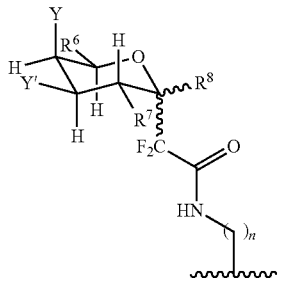

in which: n is an integer between 3 and 4,

Y, Y' are independent groups in which Y, Y'=H, OR, $N_3$, NR'R", SR''', where R=H, benzyl, trimethylsilyl, tert-butyldimethylsilyl, tert-butyldiphenylsilyl, or acetate group, R', R" independently=H, alkyl, allyl, Bn, tosylate, C(=O)-alkyl, or C(=O)—Bn, R'''=H, alkyl, or acetate group, $R^6$ is selected from H, $CH_3$, $CH_2OH$, or $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, if $R^2=R^3=H$ or $CH_3$, then $R^1=$

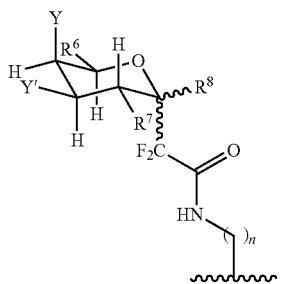

in which: n is an integer between 3 and 4,

Y, Y' are independent groups in which Y, Y'H, OR, $N_3$, NR'R", or SR''', where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'''=H, alkyl, or acetate group, $R^6$ is selected from H, $CH_3$, $CH_2OH$, or $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom or a free or protected alcohol function.

In an embodiment, the compound of formula I is a compound of formula III:

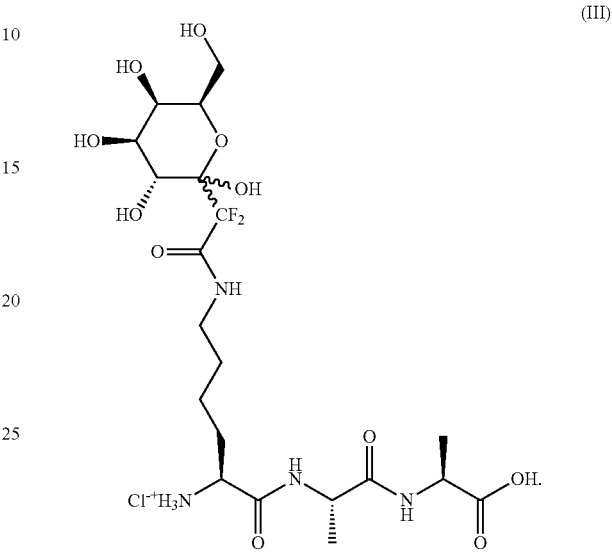

Contacting the isolated neurosensory precursor cells is with from about from about 0.01 mg/ml to about 5 mg/ml, or about 1 mg/ml to about 5 mg/ml, or 1 mg/ml to about 3 mg/ml, or from about 3 mg/ml to about 5 mg/ml of the compound of formula I, formula II or formula III.

According to another embodiment, there is disclosed an isolated neurosensory precursor cells prepared according to the method of the present invention.

According to another embodiment, there is disclosed a method of transplanting neurosensory precursor cells in a subject in need thereof comprising the steps of:

a) transplanting an isolated neurosensory precursor cells prepared according to the method of the present invention, in the subject in need thereof.

According to another embodiment, there is disclosed a method of treating a retinal degenerative disease comprising the step of:

a) transplanting an isolated neurosensory precursor cell prepared according to the method of the present invention, in the subject in need thereof.

In embodiments, the immunosuppressant drug may be daclizumab, sirolimus, tacrolimus, cyclosporine, or a combination thereof.

According to another embodiment, there is disclosed a method of treating a retinal degenerative disease comprising the step of:

a) transplanting an isolated neurosensory precursor cell prepared according to the method of the present invention, in the subject in need thereof.

The retinal degenerative disease may be age-related macular degeneration (AMD), retinitis pigmentosa (RP), retinal vasculitis, or sarcoidosis.

According to another embodiment, there is provided a use of an isolated neurosensory precursor cell prepared according to the method of the present invention, for transplantation to a subject in need thereof.

According to another embodiment, there is provided a use of an isolated neurosensory precursor cell prepared according to the method of the present invention, for treatment of a retinal degenerative disease in a subject in need thereof.

The retinal degenerative disease is age-related macular degeneration (AMD), retinitis pigmentosa (RP), retinal vasculitis, or sarcoidosis.

According to another embodiment, there is provided a use of an isolated neurosensory precursor cell according to the method of the present invention, for transplantation to a subject in need thereof.

According to another embodiment, there is provided an isolated neurosensory precursor cell contacted with a gem-difluorinated C-glycopeptide compound of general formula I (above), or a pharmaceutically acceptable base, addition salt with an acid, hydrate or solvate thereof. The compound of formula I may be a compound of formula II (as shown above). The compound of formula I may be a compound of formula III (as shown above).

According to another embodiment, there is provided a use of a gem-difluorinated C-glycopeptide compound of general formula I (as shown above), or a pharmaceutically acceptable base, addition salt with an acid, hydrate or solvate thereof, for enhancing engraftment of isolated neurosensory precursor cell in a subject in need thereof.

According to another embodiment, there is provided a use of a gem-difluorinated C-glycopeptide compound of general formula I (as shown above), or a pharmaceutically acceptable base, addition salt with an acid, hydrate or solvate thereof, for protecting isolated neurosensory precursor cell from prostaglandin E2 toxicity prior to transplantation in a subject in need thereof. The formula I may be a compound of formula II (as shown above). The compound of formula I may be a compound of formula III as shown above.

According to another embodiment, there is provided a gem-difluorinated C-glycopeptide compound of general formula I (as shown above), or a pharmaceutically acceptable base, addition salt with an acid, hydrate or solvate thereof, for use in enhancing engraftment of an isolated neurosensory precursor cell in a subject in need thereof. The formula I may be a compound of formula II (as shown above). The compound of formula I may be a compound of formula III as shown above.

According to another embodiment, there is provided a gem-difluorinated C-glycopeptide compound of general formula I, or a pharmaceutically acceptable base, addition salt with an acid, hydrate or solvate thereof, for protecting isolated neurosensory precursor cell from prostaglandin E2 toxicity prior to transplantation in a subject in need thereof. The formula I may be a compound of formula II (as shown above). The compound of formula I may be a compound of formula III as shown above. The compound of formula I, II or III may be washed away to be remove from the isolated neurosensory precursor cell.

The invention includes the compounds as shown, and also includes (where possible) individual diastereomers, enantiomers, and epimers of the compounds, and mixtures of diastereomers and/or enantiomers thereof including racemic mixtures. Although the specific stereochemistries disclosed herein are preferred, other stereoisomers, including diastereomers, enantiomers, epimers, and mixtures of these may also be useful. Inactive or less active diastereoisomers and enantiomers are useful for scientific studies relating to the targets and/or the mechanism of activation.

The compounds disclosed herein may be used in pharmaceutical compositions comprising (a) the compound(s) or pharmaceutically acceptable salts thereof, and (b) a pharmaceutically acceptable carrier. The compounds may be used in pharmaceutical compositions that include one or more other active pharmaceutical ingredients. The compounds may also be used in pharmaceutical compositions in which the compound of Formula I, II or III, or a pharmaceutically acceptable salt thereof is the only active ingredient.

Compounds of structural Formula I, structural Formula II and/or structural Formula III may contain one or more asymmetric centers and can thus occur as racemates and racemic mixtures, single enantiomers, diastereomeric mixtures and individual diastereomers. The present invention is meant to comprehend all such isomeric forms of the compounds of structural Formula I, structural Formula II and/or structural Formula III.

Compounds of structural Formula I, structural Formula II and/or structural Formula III may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural Formula I, structural Formula II and/or structural Formula III may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of generic Formula I, Formula II and/or Formula III, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I, Formula II and/or Formula III. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I, Formula II and/or Formula III can be prepared without undue experimentation by conventional techniques well known to those skilled in the art.

Salts and Formulations

It will be understood that, as used herein, references to the compounds of structural Formula I, Formula II and/or Formula III are meant to also include the pharmaceutically acceptable salts, and also salts that are not pharmaceutically acceptable when they are used as precursors to the free compounds or their pharmaceutically acceptable salts or in other synthetic manipulations. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural Formula I, Formula II and/or Formula III are included in the present invention as well.

According to an embodiment, the compounds of structural Formula I, Formula II and/or Formula III may be included in various formulations for use as medicaments.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the the partial esters with ethylene oxide, for example polyoxyethylene sorbitan monooleate. The emulsions may also contain sweetening and flavouring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

According to an embodiment, the cells are isolated using methods known in the art for their preparation. For example, the cells may be isolated from donors using mixtures of enzymes such as Collagenase I and Collagenase II, Thermolysin, non-clostridial neutral protease, or other enzymes being used for such purpose. The isolated cells may then be cultured under normal tissue culture conditions in standard tissue culture flasks.

According to an embodiment, the neurosensory precursor cells may be treated with a gem-difluorinated C-glycopeptide compound of general formula I—preferably, the compound of Formula II, and most preferably the compound of formula III in concentrations varying from about 0.01 mg/ml to about 5 mg/ml; or from about 0.1 mg/ml to about 5 mg/ml; or from about 0.5 mg/ml to about 5 mg/ml; or from about 1 mg/ml to about 5 mg/ml; or from about 3 mg/ml to about 5 mg/ml; or from about 0.01 mg/ml to about 3 mg/ml, or from about 0.1 mg/ml to about 3 mg/ml, or from about 0.5 mg/ml to about 3 mg/ml, or from about 1 mg/ml to about 3 mg/ml, or from about 0.01 mg/ml to about 1 mg/ml, or from about 0.1 mg/ml to about 1 mg/ml; or from about 0.5 mg/ml to about 1 mg/ml; or from about 0.01 mg/ml to about 0.5 mg/ml; or from about 0.1 mg/ml to about 0.5 mg/ml; or from about 0.01 mg/ml to about 0.1 mg/ml; or about 3 mg/ml. According to embodiments, the amounts above are considered to be therapeutically effective amounts for the purpose of the present inventions.

According to another embodiment, the cells are contacted with the gem-difluorinated C-glycopeptide compound for a time sufficient to effect improvements on cell viability and survival rate. According to embodiments, the time sufficient may be from about 12 hours to 120 hours, or from about 12 hours to about 96 hours, or from about 12 hours to about 72 hours, or from about 12 hours to about 48 hours, or from about 12 hours to about 24 hours, or about 120 hours, or about 96 hours, or about 72 hours, or about 48 hours, or about 24 hours, or about 12 hours, or about 10 hours, or about 8 hours, or about 6 hours, or about 4 hours, or about 2 hours, or about 1 hour. In embodiments, the wherein the isolated neurosensory precursor cell is contacted with the compound for 1 hour, 55 mins, 50 mins, 45 mins, 40 mins, 35 mins, 30 mins, 25 mins, 20 mins, 15 mins, 10 mins, 5 mins, 4 mins, 3 mins, 2 mins, 1 mins, 45 secs, or 30 secs, or at least 1 hour, or at least 55 mins, or at least 50 mins, or at least 45 mins, or at least 40 mins, or at least 35 mins, or at least 30 mins, or at least 25 mins, or at least 20 mins, or at least 15 mins, or at least 10 mins, or at least 5 mins, or at least 4 mins, or at least 3 mins, or at least 2 mins, or at least 1 mins, or at least 45 secs, or at least 30 secs.

In another embodiment there is disclosed a cell preparation prepared according to the method of the present invention, in a pharmaceutically acceptable carrier. According to an embodiment, the cell preparation may be used for the preparation of a medicament for a cell transplantation. According to another embodiment, the cell preparation may be used for a cell transplantation.

In another embodiment, there is disclosed a method of transplantation comprising transplanting a cell preparation of the present invention to a subject in need thereof. The subject may be a mammal, and preferably a human.

The present invention will be more readily understood by referring to the following examples which are given to illustrate the invention rather than to limit its scope.

EXAMPLE 1

To identify the key factors that inhibit NPC integration into diseased tissue, an ex vivo tissue culture system has been developed to enable the identification of factors that reduce and factors that enhance cell survival and functional integration (Yanai et al., 2015). The ex vivo system mimics the subretinal space in a regulated environment that includes a neurosensory retinal explant placed on top of human embryonic stem cells (hESC) derived retinal pigment epithelium (RPE). NPCs (such as human photoreceptor precursor cells; PPCs, Yanai et al., 2013) can then be placed within the model in a more controlled environment. Thus the role of adverse factors such as nutritional deficits and toxic metabolites can be studied in isolation from other hostile effects such as surgical trauma and immune rejection. It is hypothesized that toxic metabolites, such as PGE2, are major adverse factors during tissue transplantation in necrotic neurodegeneration of the retina. Furthermore, AAGP™ is selected as a potential protective agent, and its ability to prevent PGE2 toxic effects is examined. AAGP™ is a small, stable, synthetic analog of anti-freeze protein (AFP) which has been shown to protect cells for example, against exposure to extreme temperatures and ultraviolet irradiation (US Patent publication No. US20090311203).

Now referring to FIG. 1, within the ex vivo system, rat neurosensory retinal explants are incubated upon human embryonic stem cells (hESC) derived retinal pigment epithelium (RPE). Neurosensory retina was obtained from the S334ter-4 model of retinal degeneration (Chen et al, 1995) and cultured within the system for 10 days (for detailed experimental design see Yanai et al., 2015). Rodent retinal tissue collection was carried out with approval of the Animal Care Committee at the University of British Columbia and in accordance with the Association for Research in Vision and Ophthalmology Statement for the Use of Animals in Ophthalmic and Vision Research. Throughout the present study, AAGP™ was used at 4 mg/ml, after it was confirmed it was not toxic to PPCs at this concentration (unpublished data).

Firstly, the amount of PGE2 produced is determined within the ex vivo system under normal culture conditions and after media is supplemented with 4 mg/ml AAGP for the first 24 hours of co-culture. Three equal-sized retinal quadrants, measuring ~10 mm$^2$ each, and are analyzed for each condition. Explant media are collected at the end of 10 days and assessed for concentration of PGE2 by enzyme-linked immunosorbent assay (ELISA; R&D Systems). PGE2 induced reduction in metabolic activity, contributing to cell death, is assessed in PPCs cultured in isolation using a Thiazolyl Blue Tetrazolium Bromide (MTT) assay (Sigma).

To determine whether AAGP™ inhibits COX-2 expression, ARPE-19 cells (Dunn et al., 1996) are treated with 17 ng/ml Interleukin 1β (IL-1β; Sigma; Lukiw et al., 2006) for 8 hours and then added 5 mM ATP for 1 hour to further induce cell stress (Sigma; Mehta et al., 2001). ARPE-19 is a human retinal pigment epithelia (RPE) cell line spontaneously arising from a primary culture of RPE cells from a male donor. These cells have many morphological and some functional similarities with authentic RPE. Experiments are conducted either in the presence or absence of 4 mg/ml AAGP™. COX-2 expression is assessed using Reverse Transcription Quantitative Polymerase Chain Reaction (RT-qPCR) with the TaqMan® primer/probe system, Fast Advanced Master Mix and the ViiA™ 7 Real Time PCR system (Applied Biosystems).

To determine whether AAGP™ improves PPC survival in the ex vivo system, PPC cell viability is assessed with and without pre-treating cell grafts with AAGP™ for 24 hours prior to inclusion within the ex vivo system. PPCs are labelled with 20 µM CellTrace™ Far Red DDAO-SE (Life Technologies). DDAO-SE is a fixable, far-red fluorescent tracer for long-term cell labeling. The tracer is colorless and non-fluorescent until its acetate groups are cleaved by intracellular esterases to yield highly fluorescent products. DDAO-SE forms a strong covalent attachment to primary amines on proteins and other biomolecules and is therefore not likely to transfer to other types of cells in the co-culture. In each experiment (n=4), between 2 and 4 retinal explants are used for each condition ('technical repeats'). About 350,000 labeled PPCs are used in each technical repeat. After 10 days, the components of the co-culture system are enzymatically dissociated into single cell suspensions and the number of viable PPCs is assessed by Fluorescence-Activated Cell Sorting (FACS; Influx Sorter; BD Biosciences).

For statistical analyses an unpaired Student's t-test is performed. P values of less than 0.05 are considered significant.

Figure 2:
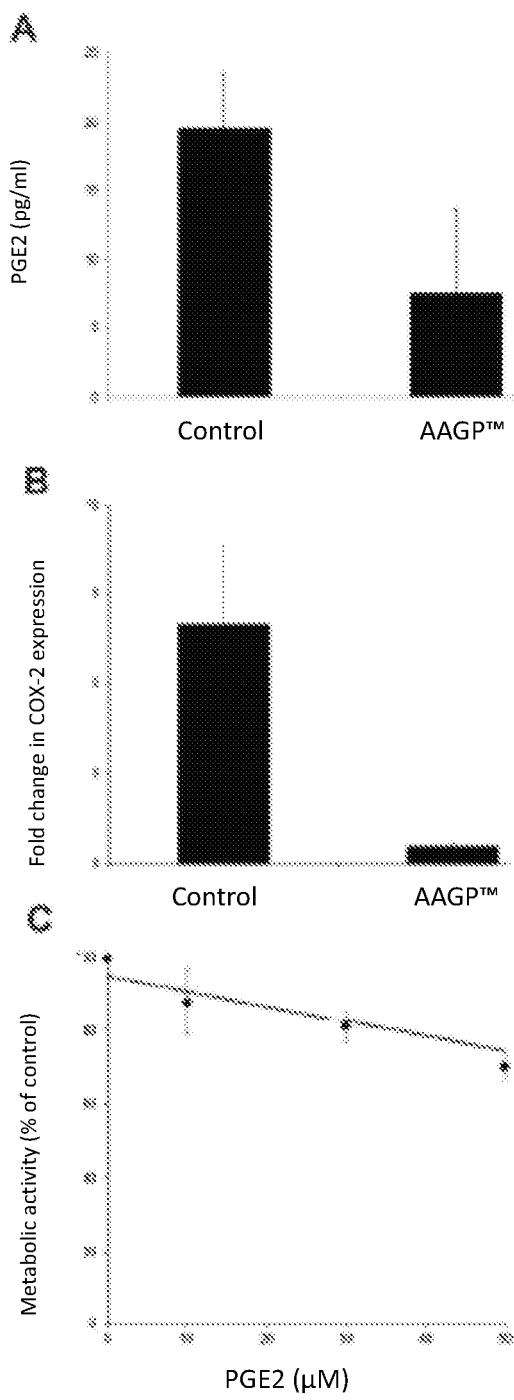
FIG. 2 illustrates that AAGP™ reduces the amount of prostaglandin E2 (PGE2) secreted by degenerating explants and the level of COX-2 expression. PGE2 is toxic to photoreceptor precursor cells (PPCs). (A) Rat retinal explants were cultured in explant medium with or without 4 mg/ml AAGP (n=3 for each condition). Explant media was replaced after 24 hours and replenished every other day with medium not containing AAGP. After ten days, explant medium was collected and processed for PGE2 ELISA. Histograms represent the amount of PGE2 (pg/ml) present in the explant medium. (B) COX-2 expression was assessed by RT-qPCR in stressed ARPE-19 cells in the presence or absence of 4 mg/ml AAGP (n=4). Histograms represent fold change in COX-2 expression, normalized to GAPDH. (C) Cultured PPCs were treated with increasing amounts of PGE2 for 48 hours, followed by the MTT assay (n=4). The effect on PPCs' metabolic activity was plotted as a function of PGE2 concentrations.

The results demonstrate that following 10 days of co-culture, the explant medium contained ~20 pg/ml of PGE2, and when AAGP™ is present for the first day, the amount of PGE2 decreased to ~7.5 pg/ml (n=3; p<0.05; FIG. 2A).

A plausible reason for the reduced level of PGE2 in the presence of AAGP™ is that COX-2 levels are downregulated by this compound. COX-2 is induced by inflammatory stimuli and its expression is likely chronic in the explant system, making it difficult to detect small changes in expression levels. Therefore, COX-2 expression is assessed in cultured cells, responding to an acute stress, where the effect is maximized. COX-2 downregulation is confirmed in an ARPE-19 cell stress assay using IL-1β followed by ATP. COX-2 expression is evident in stressed cells but this expression declined by at least 13.3±4.5 fold, to negligible levels, in the presence of AAGP™ (n=4; FIG. 2B). To examine whether PGE2 is toxic to cells, PPCs are cultured for 48 hours in retinal differentiation medium supplemented with increasing amounts of PGE2 (up to 50 µM) and analyzed cells survival by the MTT assay (n=4). Cell survival is reduced by up to 44% (FIG. 2C), confirming PGE2 toxicity.

Figure 3:
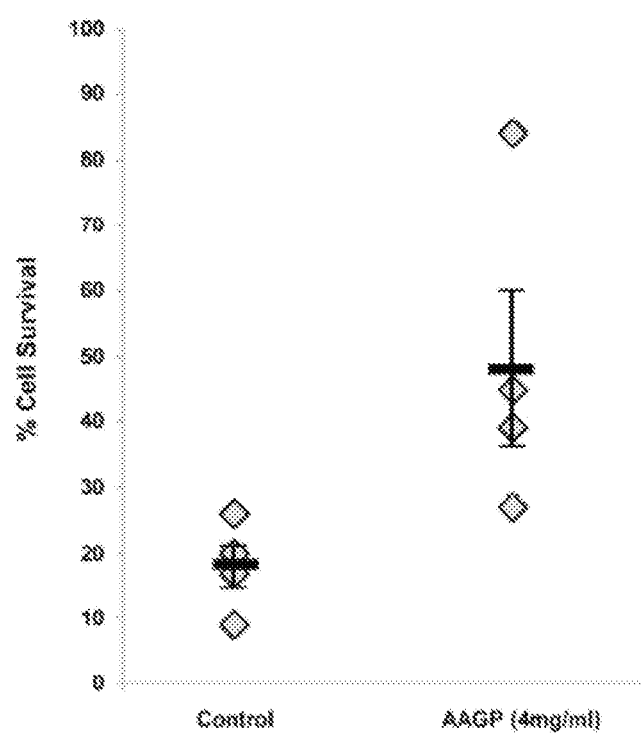
FIG. 3 illustrates that Cell survival is enhanced by pre-incubation with AAGP™. Untreated or AAGP™-treated PPCs are fluorescently labelled and placed between retinal explants and RPE for ten days (n=4). Live PPCs are separated by Fluorescence-Activated Cell Sorting and the proportion of cells surviving after 10 days of co-culture was calculated. Percent cell survival of untreated and AAGP-treated PPCs was plotted (◆) and for each condition the average±SEM is represented by a thick black line.

Finally, the viability of PPCs in the ex vivo system is tested. Untreated PPCs or PPCs pre-treated for 24 hours with 4 mg/ml AAGP™ are labelled with a fluorescent live cell tracer and ~350,000 PPCs are placed in-between the explant and RPE. Ten days later, the co-cultured components were dissociated into single cells and viable PPCs (labeled red) were separated by Fluorescence activated cell sorting (FACS, FIG. 3). The proportion of live cells remaining after 10 days of co-culture is calculated. An almost 3-fold increase in average cell viability is obtained when PPCs are pre-treated with AAGP™ for 24 hours before "transplantation" (49% vs. 18%; p<0.05).

Altogether the results presented in this study indicate that NPCs, such as PPCs, transplanted into neurological tissue may, in part, die as a result from exposure to PGE2 released from host necrotic tissue, such necrosis is a cause of retinal degenerations such as retinal detachment. Targeting toxic by-products such as PGE2 therefore appears to surprisingly and unexpectedly be a valid option to improve survival of transplanted precursor cells. The data presented here suggests that AAGP™ may have a role in inhibiting PGE2 production in necrotic tissue ex vivo.

The ex vivo system presented herein appears to be an appropriate screening method to identify valid therapeutics to move into more labor intensive in vivo studies. These results also suggest that other inhibitors of COX2, such as non-steroidal anti-inflammatory drugs, may likewise enhance survival of transplanted NPCs during cell transplantation experiments.

While preferred embodiments have been described above and illustrated in the accompanying drawings, it will be evident to those skilled in the art that modifications may be made without departing from this disclosure. Such modifications are considered as possible variants comprised in the scope of the disclosure.

REFERENCES

Cavassani K A, Ishii M, Wen H, Schaller M A, Lincoln P M, Lukacs N W, Hogaboam C M and Kunkel S L. 2008. TLR3 is an endogenous sensor of tissue necrosis during acute inflammatory events. J Exp Med, 205(11):2609-2621.

Chen J, Makino C L, Peachey N S, Baylor D A and Simon M I. 1995, Mechanisms of rhodopsin inactivation in vivo as revealed by a COOH-terminal truncation mutant. Science 267: 374-377

Dunn K C, Aotaki-Keen A E, Putkey F R and Hjelmeland L M. 1996, ARPE-19, a human retinal pigment epithelial cell line with differentiated properties. Exp Eye Res, 62: 155-169.

Klassen H. 2015, Stem cells in clinical trials for treatment of retinal degeneration. Expert Opin Biol Ther. DOI: 10.1517/14712598.2016.1093110

Lukiw W J, Pranab K. Mukherjee P K, Cui J G and Nicolas G. Bazan. 2006, A2E Selectively Induces COX-2 in ARPE-19 and Human Neural Cells. Current Eye Research, 31:259-263

Ma J, Kabiel M, Tucker B A, Ge J, Young M J. 2011, Combining chondroitinase ABC and growth factors promotes the integration of murine retinal progenitor cells transplanted into Rho(−/−) mice. Mol Vis. 17:1759-1770

Mehta V B, Hart J and Wewers M D. 2001, ATP-stimulated Release of Interleukin (IL)-1b and IL-18 Requires Priming by Lipopolysaccharide and Is Independent of Caspase-1 Cleavage. J Biol Chem 276(6): 3820-3826

Miyagishi H, Kosuge Y, Yoneoka Y, Ozone M, Endo M, Osada N, Ishige K, Kusama-Eguchi K and Ito Y. 2013, Prostaglandin E2-Induced Cell Death is Mediated by Activation of EP2 Receptors in Motor Neuron-like NSC-34 Cells. J Pharmacol Sci 121: 347-350

Ricciotti E and FitzGerald G A. 2011. Prostaglandins and Inflammation. Arterioscler Thromb Vasc Biol, 31(5): 986-1000 Scaffidi P, Misteli T and Bianchi M E. 2002, Release of chromatin protein HMGB1 by necrotic cells triggers inflammation. Nature 418(6894): 191-195.

Singh, M S, Charbel Issa, P, Butler, R, Martin, C, Lipinski, D M, Sekaran, S, Barnard, A R and MacLaren, R E. 2013. Reversal of end-stage retinal degeneration and restoration of visual function by photoreceptor transplantation. Proc Natl Acad Sci USA, 110(3): 1101-1106 Stone L L, Grande A and Low W C. 2013, Neural Repair and Neuroprotection with Stem Cells in Ischemic Stroke. Brain Sci, 3: 599-614

Takadera T, Shiraishi Y and Ohyashiki T. 2004, Prostaglandin E2 induced caspasedependent apoptosis possibly through activation of EP2 receptors in cultured hippocampal neurons. Neurochemistry International, 45: 713-719

Tovar-Y-Romo L B, Penagos-Puig A and Ramirez-Jarquin

J O. 2016, Endogenous recovery after brain damage: molecular mechanisms that balance neuronal life/death fate. J Neurochem. 136(1): 13-27

Warre-Comish, K, Barber, A C, Sowden, J C, Ali, R R and Pearson R A. 2014, Migration, integration and maturation of photoreceptor precursors following transplantation in the mouse retina. Stem Cells Dev, 23: 941-954 West E L, Gonzalez-Cordero A, Hippert C, Osakada F, Martinez-Barbera, J P, Pearson R A, Sowden J C, Takahashi M, and Ali R R. 2012, Defining the integration capacity of embryonic stem cell-derived photoreceptor precursors. Stem Cells, 30(7): 1424-1435

Yanai A, Laver C R, Joe A W, Viringipurampeer I A, Wang X, Gregory-Evans C Y and Gregory-Evans K. 2013, Differentiation of human embryonic stem cells using sizecontrolled embryoid bodies and negative cell selection in the production of photoreceptor precursor cells. Tissue Eng Part C: Methods, 19: 755-764

Yanai A, Laver C R, Gregory-Evans C Y, Liu R R and Gregory-Evans K. 2015, Enhanced functional integration of human photoreceptor precursors into human and rodent retina in an ex vivo retinal explant model system. Tissue Eng Part A, 21: 1763-1771

Zhou W and Yuan J. 2014, Necroptosis in health and diseases. Semin Cell Dev Biol. 35: 14-23.

The invention claimed is:

1. A method for enhancing engraftment of neurosensory precursor cells comprising the step of:

a) contacting an isolated neurosensory precursor cell prior to a transplantation in a subject in need thereof, with a gem-difluorinated C-glycopeptide compound of general formula I, or a pharmaceutically acceptable base, addition salt with an acid, hydrate or solvate thereof, and then washing the isolated neurosensory precursor cell to remove the compound:

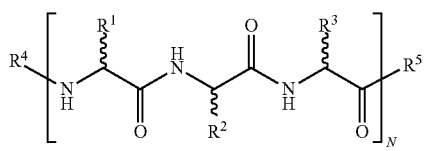

(I)

in which:

N is an integer between 1 and 5, $R^4$=H, $AA_1$, or $AA_1$-$AA_2$, $R^5$=OH, $AA_1$, or $AA_1$-$AA_2$, $AA_1$ and $AA_2$ independently represent amino acids with a non-polar side chain and $R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$ and the remaining $R^1$, $R^2$, $R^3$ is

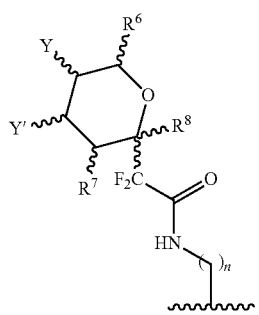

in which:

n is an integer between 3 and 4,

Y, Y' are independent groups in which Y, Y'=H, OR, $N_3$, NR'R", or SR''', where R=H, benzyl, trimethylsilyl, tert-butyldimethylsilyl, tert-butyldiphenylsilyl or acetate group, R', R" independently=H, alkyl, allyl, benzyl, tosylate group, C(=O)-alkyl or C(=O)—Bn, R'''=H, alkyl, or acetate group, $R^6$ is H, $CH_3$, $CH_2OH$, $CH_2$-glycoside group or $CH_2$—OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP' or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, and if $R^1$=$R^2$=H, $CH_3$, $CH_2Ph$, $CH(CH_3)_2$, $CH_2CH(CH_3)_2$, or $CH(CH_3)CH_2CH_3$ then $R^3$=

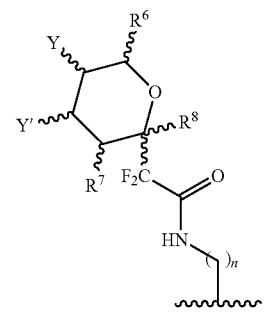

in which: n is an integer between 3 and 4,

Y, Y' are independent groups in which Y, Y'=H, OR, $N_3$, NR'R", or SR''', where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'''=H, alkyl, or acetate group, $R^6$ is H, $CH_3$, $CH_2OH$, $CH_2$-glycoside group, or $CH_2$—OGP in which GP is a protector group selected from alkyl, benzyl, trimethylsilyl, tertbutyldimethylsilyl, tert-butyldiphenylsilyl, or acetate group, R⁷=OH, OGP', NH₂, N₃, NHGP', or NGP'GP" in which GP' and GP" are independently selected from alkyl, benzyl, trimethylsilyl, tertbutyldimethylsilyl, tert-butyldiphenylsilyl, or acetate group, R⁸ is a hydrogen atom H or a free or protected alcohol function, if R¹=R³=H, CH₃, CH₂Ph, CH(CH₃)₂, CH₂CH(CH₃)₂, or CH(CH₃)CH₂CH₃ then R²=

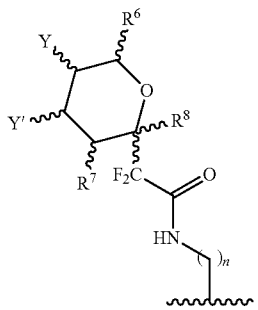

in which: n is an integer between 3 and 4,

Y, Y' are independent groups in which Y, Y'=H, OR, N₃, NR'R", or SR'", where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'"=H, alkyl, or acetate group, R⁶ is H, CH₃, CH₂OH, CH₂-glycoside group, or CH₂—OGP in which GP is a protector group selected from alkyl, benzyl, trimethylsilyl, tert-butyldimethylsilyl, tert-butyldiphenylsilyl, or acetate group, R⁷=OH, OGP', NH₂, N₃, NHGP', or NGP'GP" in which GP' and GP" are independently selected from alkyl, benzyl, trimethylsilyl, tertbutyldimethylsilyl, tert-butyldiphenylsilyl, or acetate group, R⁸ is a hydrogen atom H or a free or protected alcohol function, if R²=R³=H, CH₃, CH(CH₃)₂, CH₂CH(CH₃)₂, or CH(CH₃)CH₂CH₃ then R¹=

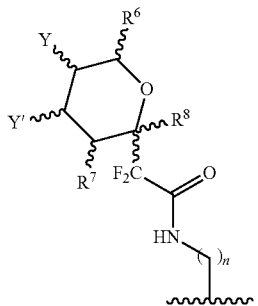

in which: n is an integer between 3 and 4,

Y, Y' are independent groups in which Y, Y'H, OR, N₃, NR'R", or SR'", where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'"=H, alkyl, or acetate group, R⁶ is H, CH₃, CH₂OH, CH₂-glycoside group, or CH₂—OGP in which GP is a protector group selected from alkyl, benzyl, trimethylsilyl, tert-butyldimethylsilyl, tert-butyldiphenylsilyl, or acetate group, R⁷=OH, OGP', NH₂, N₃, NHGP', or NGP'GP" in which GP' and GP" are independently selected from alkyl, benzyl, trimethylsilyl, tertbutyldimethylsilyl, tert-butyldiphenylsilyl, or acetate group, R⁸ is a hydrogen atom H or a free or protected alcohol function; and b) transplanting the treated isolated neurosensory precursor cells of step a) in a subject in need thereof, wherein the method comprises no step where said isolated neurosensory precursor cells are cryopreserved.

2. The method of claim 1, wherein the compound of formula I is a compound of formula II:

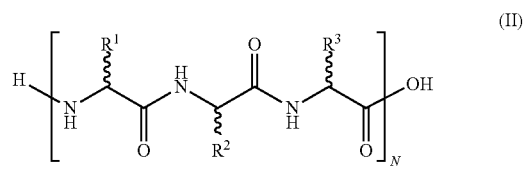

(II)

in which: N is an integer between 1 and 5, and

R¹, R², R³ are independent groups in which two of R¹, R² and R³ are selected from H, CH₃ and the remaining R¹, R² and R³ is

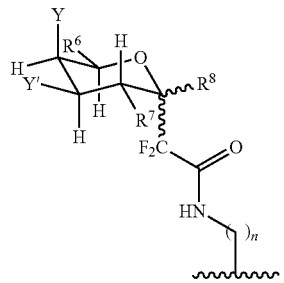

in which: n is an integer between 3 and 4,

Y, Y' are independent groups in which Y, Y'=H, OR, N₃, NR'R" or SR'", where R=H, benzyl, trimethylsilyl, tert-butyldimethylsilyl, tert-butyldiphenylsilyl, or acetate group, R', R" independently=H, alkyl, allyl, benzyl, tosylate group, C(=O)-alkyl, or C(=O)—Bn, R'"=H, alkyl, or acetate group, R⁶ is selected from H, CH₃, CH₂OH, CH₂—OGP in which GP is a protector group selected from alkyl, benzyl, trimethylsilyl, tert-butyldimethylsilyl, tert-butyldiphenylsilyl, or acetate group, R⁷=OH, OGP=, NH₂, N₃, NHGP', NGP'GP" in which GP' and GP" are independently selected from alkyl, benzyl, trimethylsilyl, tert-butyldimethylsilyl, tert-butyldiphenylsilyl or acetate group, R⁸ is a hydrogen atom H or a free or protected alcohol function, and
if $R^1=R^2=$H or $CH_3$,
then $R^3=$

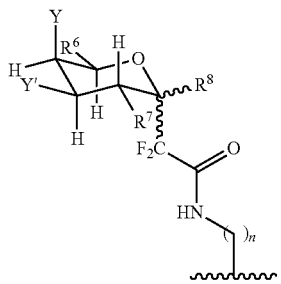

in which: n is an integer between 3 and 4,
  Y, Y' are independent groups
    in which Y, Y'=H, OR, $N_3$, NR'R'', or SR''',
      where R=H, benzyl, trimethylsilyl, tert-butyldimethylsilyl, tert-butyldiphenylsilyl, or acetate group,
    R', R' independently=H, alkyl, allyl, benzyl, tosylate group, C(=O)-alkyl,
    or
    C(=O)—Bn,
    R'''=H, alkyl, or acetate group,
  $R^6$ is selected from H, $CH_3$, $CH_2OH$, $CH_2$—OGP in which GP is a protector group selected from alkyl, benzyl, trimethylsilyl, tert-butyldimethylsilyl, tert-butyldiphenylsilyl, or acetate group,
  $R^7=$OH, OGP', $NH_2$, $N_3$, NHGP', NGP'GP'' in which GP' and GP'' are independently selected from alkyl, benzyl, trimethylsilyl, tert-butyldimethylsilyl, tert-butyldiphenylsilyl, or acetate group,
  $R^8$ is a hydrogen atom H or a free or protected alcohol function,
if $R^1=R^3=$H or $CH_3$,
then $R^2=$

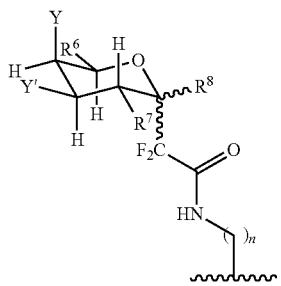

in which: n is an integer between 3 and 4,
  Y, Y' are independent groups
    in which Y, Y'=H, OR, $N_3$, NR'R'', SR''',
      where R=H, benzyl, trimethylsilyl, tert-butyldimethylsilyl, tert-butyldiphenylsilyl, or acetate group,
    R', R'' independently=H, alkyl, allyl,
    Bn, tosylate, C(=O)-alkyl, or C(=O)—Bn,
    R'''=H, alkyl, or acetate group,
  $R^6$ is selected from H, $CH_3$, $CH_2OH$, or $CH_2$—OGP in which GP is a protector group selected from alkyl, benzyl, trimethylsilyl, tert-butyldimethylsilyl, tert-butyldiphenylsilyl, or acetate group,
  $R^7 =$OH, OGP', $NH_2$, $N_3$, NHGP', or NGP'GP'' in which GP' and GP'' are independently selected from alkyl, benzyl, trimethylsilyl, tert-butyldimethylsilyl, tert-butyldiphenylsilyl, or acetate group, benzyl, trimethylsilyl, tert-butyldimethylsilyl, tert-butyldiphenylsilyl, or acetate group,
$R^8$ is a hydrogen atom H or a free or protected alcohol function,
if $R^2=R^3=$H or $CH_3$,
then $R^1=$

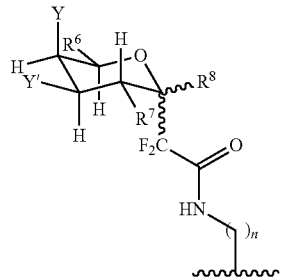

in which: n is an integer between 3 and 4,
  Y, Y' are independent groups
    in which Y, Y'H, OR, $N_3$, NR'R'', or SR''',
      where R=H, benzyl, trimethylsilyl, tert-butyldimethylsilyl, tert-butyldiphenylsilyl, or acetate group,
    R', R'' independently=H, alkyl, allyl, benzyl, tosylate group, C(=O)-alkyl, or C(=O)—Bn,
    R'''=H, alkyl, or acetate group,
  $R^6$ is selected from H, $CH_3$, $CH_2OH$, or $CH_2$—OGP in which GP is a protector group selected from alkyl, benzyl, trimethylsilyl, tert-butyldimethylsilyl, tert-butyldiphenylsilyl, or acetate group,
  $R^7=$OH, OGP', $NH_2$, $N_3$, NHGP', or NGP'GP'' in which GP' and GP'' are independently selected from alkyl, benzyl, trimethylsilyl, tert-butyldimethylsilyl, tert-butyldiphenylsilyl, or acetate group,
$R^8$ is a hydrogen atom or a free or protected alcohol function.

3. The method of claim 1, wherein said compound of formula I is a compound of formula III:

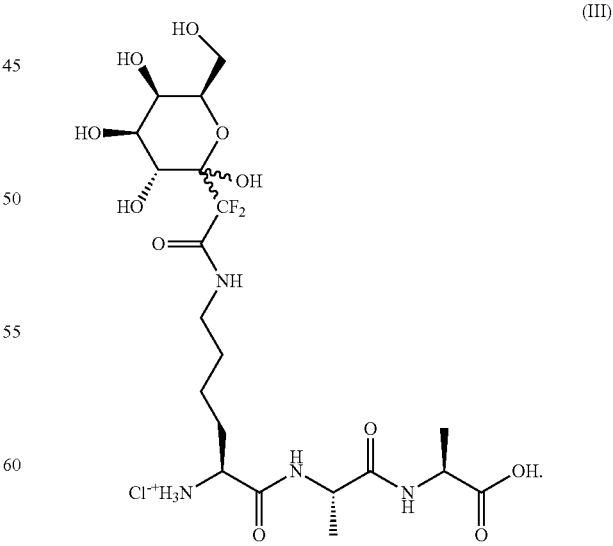

(III)

4. The method of claim 1, wherein the isolated neurosensory precursor cell is contacted with the compound for at least 1 hour.

5. The method of claim 1, wherein concentration of the compound is from about 1 mg/ml to about 5 mg/ml.

6. The method of claim 5, wherein concentration of said compound is from about 1 mg/ml to about 3 mg/ml, or from about 3 mg/ml to about 5 mg/ml.

7. The method of claim 1, wherein said neurosensory precursor cell is a photoreceptor precursor cell.

8. An isolated neurosensory precursor cell prepared according to the method of claim 1.

9. The method of claim 1, wherein said subject is receiving an immunosuppressant drug.

10. The method of claim 9, wherein the immunosuppressant drug is daclizumab, sirolimus, tacrolimus, cyclosporine, or a combination thereof.

11. The method of claim 1, wherein said subject is a human subject.

12. The method of claim 1, wherein said method is for treating a retinal degenerative disease.

13. The method of claim 12, where said retinal degenerative disease is age-related macular degeneration (AMD), retinitis pigmentosa (RP), retinal vasculitis, or sarcoidosis.

\* \* \* \* \*